(12) United States Patent
McGrane et al.

(10) Patent No.: US 10,653,332 B2
(45) Date of Patent: May 19, 2020

(54) CONDUCTIVE STIFFENER, METHOD OF MAKING A CONDUCTIVE STIFFENER, AND CONDUCTIVE ADHESIVE AND ENCAPSULATION LAYERS

(71) Applicant: MC10, Inc., Lexington, MA (US)

(72) Inventors: Bryan McGrane, Cambridge, MA (US); Milan Raj, Natick, MA (US); PingHung Wei, Burlingame, MA (US); Briana Morey, Somerville, MA (US); Roozbeh Ghaffari, Cambridge, MA (US); Monica Lin, San Jose, CA (US); Jeffrey Model, Cambridge, MA (US); Xianyan Wang, San Jose, CA (US); Bryan Keen, Somerville, MA (US); Stephen Lee, Ann Arbor, MI (US)

(73) Assignee: MC10, Inc., Lexington, MA (US)

( * ) Notice: Subject to any disclaimer, the term of this patent is extended or adjusted under 35 U.S.C. 154(b) by 473 days.

(21) Appl. No.: 15/208,444

(22) Filed: Jul. 12, 2016

(65) Prior Publication Data

US 2017/0019988 A1 Jan. 19, 2017

Related U.S. Application Data

(60) Provisional application No. 62/194,058, filed on Jul. 17, 2015.

(51) Int. Cl.
*H05K 1/18* (2006.01)
*H05K 1/02* (2006.01)
(Continued)

(52) U.S. Cl.
CPC .......... *A61B 5/0496* (2013.01); *A61B 5/0408* (2013.01); *A61B 5/0476* (2013.01);
(Continued)

(58) Field of Classification Search
CPC .......... H05K 1/189; H05K 2201/2009; H05K 2201/0969; H05K 2203/1327
See application file for complete search history.

(56) References Cited

U.S. PATENT DOCUMENTS 3,716,861 A 2/1973 Root
3,805,427 A 4/1974 Epstein
(Continued)

FOREIGN PATENT DOCUMENTS

EP 0585670 A2 3/1994
EP 0779059 A1 6/1997
(Continued)

OTHER PUBLICATIONS

International Search Report dated Dec. 9, 2016 which issued in International Patent Application No. PCT/US2016/041927 (5 pages).
(Continued)

*Primary Examiner* — Nathan Milakovich
(74) *Attorney, Agent, or Firm* — Nixon Peabody LLP

(57) ABSTRACT

A device includes a flexible printed circuit board and one or more conductive stiffeners. The conductive stiffeners include a conductive surface that can be electrically connected to contact pads on the flexible printed circuit board. The wearable device can further include an adhesive layer or an encapsulation layer. The adhesive layer and the encapsulation layer can include conductive portions surrounded by non-conductive portions. The conductive portions can be aligned with the conductive stiffeners and together transmit electrical energy to the contact pads of the flexible printed circuit board.

31 Claims, 10 Drawing Sheets

(51) Int. Cl.
*A61B 5/0496* (2006.01)
*A61B 5/00* (2006.01)
*A61B 5/0476* (2006.01)
*A61B 5/0488* (2006.01)
*A61B 5/0492* (2006.01)
*A61B 5/0478* (2006.01)
*A61B 5/0408* (2006.01)
*A61B 5/01* (2006.01)
*A61B 5/0402* (2006.01)
*A61B 5/053* (2006.01)

(52) U.S. Cl.
CPC .......... *A61B 5/0478* (2013.01); *A61B 5/0488* (2013.01); *A61B 5/0492* (2013.01); *A61B 5/6801* (2013.01); *H05K 1/189* (2013.01); *A61B 5/01* (2013.01); *A61B 5/0402* (2013.01); *A61B 5/053* (2013.01); *A61B 2562/164* (2013.01); *A61B 2562/166* (2013.01); *H05K 1/0209* (2013.01); *H05K 1/0283* (2013.01); *H05K 2201/0969* (2013.01); *H05K 2201/10106* (2013.01); *H05K 2201/10151* (2013.01); *H05K 2201/10401* (2013.01); *H05K 2201/2009* (2013.01); *H05K 2203/1327* (2013.01)

(56) References Cited

U.S. PATENT DOCUMENTS

| | | |
|---|---|---|
| 3,838,240 A | 9/1974 | Schelhorn |
| 4,278,474 A | 7/1981 | Blakeslee |
| 4,304,235 A | 12/1981 | Kaufman |
| 4,416,288 A | 11/1983 | Freeman |
| 4,658,153 A | 4/1987 | Brosh |
| 5,214,000 A | 5/1993 | Chazan |
| 5,272,375 A | 12/1993 | Belopolsky |
| 5,306,917 A | 4/1994 | Black |
| 5,326,521 A | 7/1994 | East |
| 5,331,966 A | 7/1994 | Bennett |
| 5,360,987 A | 11/1994 | Shibib |
| 5,471,982 A | 5/1995 | Edwards |
| 5,454,270 A | 10/1995 | Brown |
| 5,491,651 A | 2/1996 | Janic |
| 5,567,975 A | 10/1996 | Walsh |
| 5,580,794 A | 12/1996 | Allen |
| 5,617,870 A | 4/1997 | Hastings |
| 5,811,790 A | 9/1998 | Endo |
| 5,817,008 A | 10/1998 | Rafert |
| 5,907,477 A | 5/1999 | Tuttle |
| 6,063,046 A | 5/2000 | Allum |
| 6,265,090 B1 | 7/2001 | Nishide |
| 6,282,960 B1 | 9/2001 | Samuels |
| 6,343,514 B1 | 2/2002 | Smith |
| 6,387,052 B1 | 5/2002 | Quinn |
| 6,410,971 B1 | 6/2002 | Otey |
| 6,421,016 B1 | 7/2002 | Phillips |
| 6,455,931 B1 | 9/2002 | Hamilton |
| 6,567,158 B1 | 5/2003 | Falcial |
| 6,626,940 B2 | 9/2003 | Crowley |
| 6,641,860 B1 | 11/2003 | Kaiserman |
| 6,775,906 B1 | 8/2004 | Silverbrook |
| 6,784,844 B1 | 8/2004 | Boakes |
| 6,965,160 B2 | 11/2005 | Cobbley |
| 6,987,314 B1 | 1/2006 | Yoshida |
| 7,259,030 B2 | 8/2007 | Daniels |
| 7,265,298 B2 | 9/2007 | Maghribi |
| 7,302,751 B2 | 12/2007 | Hamburgen |
| 7,337,012 B2 | 2/2008 | Maghribi |
| 7,487,587 B2 | 2/2009 | Vanfleteren |
| 7,491,892 B2 | 2/2009 | Wagner |
| 7,521,292 B2 | 4/2009 | Rogers |
| 7,557,367 B2 | 7/2009 | Rogers |
| 7,618,260 B2 | 11/2009 | Daniel |
| 7,622,367 B1 | 11/2009 | Nuzzo |
| 7,727,228 B2 | 6/2010 | Abboud |
| 7,739,791 B2 | 6/2010 | Brandenburg |
| 7,759,167 B2 | 7/2010 | Vanfleteren |
| 7,815,095 B2 | 10/2010 | Fujisawa |
| 7,960,246 B2 | 6/2011 | Flamand |
| 7,982,296 B2 | 7/2011 | Nuzzo |
| 8,097,926 B2 | 1/2012 | De Graff |
| 8,198,621 B2 | 6/2012 | Rogers |
| 8,207,473 B2 | 6/2012 | Axisa |
| 8,217,381 B2 | 7/2012 | Rogers |
| 8,372,726 B2 | 2/2013 | De Graff |
| 8,389,862 B2 | 3/2013 | Arora |
| 8,431,828 B2 | 4/2013 | Vanfleteren |
| 8,440,546 B2 | 5/2013 | Nuzzo |
| 8,536,667 B2 | 9/2013 | De Graff |
| 8,552,299 B2 | 10/2013 | Rogers |
| 8,618,656 B2 | 12/2013 | Oh |
| 8,664,699 B2 | 3/2014 | Nuzzo |
| 8,679,888 B2 | 3/2014 | Rogers |
| 8,729,524 B2 | 5/2014 | Rogers |
| 8,754,396 B2 | 6/2014 | Rogers |
| 8,865,489 B2 | 10/2014 | Rogers |
| 8,886,334 B2 | 11/2014 | Ghaffari |
| 8,905,772 B2 | 12/2014 | Rogers |
| 9,012,784 B2 | 4/2015 | Arora |
| 9,082,025 B2 | 7/2015 | Fastert |
| 9,105,555 B2 | 8/2015 | Rogers |
| 9,105,782 B2 | 8/2015 | Rogers |
| 9,119,533 B2 | 9/2015 | Ghaffari |
| 9,123,614 B2 | 9/2015 | Graff |
| 9,159,635 B2 | 10/2015 | Elolampi |
| 9,168,094 B2 | 10/2015 | Lee |
| 9,171,794 B2 | 10/2015 | Rafferty |
| 9,186,060 B2 | 11/2015 | De Graff |
| 9,226,402 B2 | 12/2015 | Hsu |
| 9,247,637 B2 | 1/2016 | Hsu |
| 9,289,132 B2 | 3/2016 | Ghaffari |
| 9,295,842 B2 | 3/2016 | Ghaffari |
| 9,324,733 B2 | 4/2016 | Rogers |
| 9,372,123 B2 | 6/2016 | Li |
| 9,408,305 B2 | 8/2016 | Hsu |
| 10,321,561 B2* | 6/2019 | Hu ............. H05K 1/0281 |
| 2001/0012918 A1 | 8/2001 | Swanson |
| 2001/0021867 A1 | 9/2001 | Kordis |
| 2002/0026127 A1 | 2/2002 | Balbierz |
| 2002/0082515 A1 | 6/2002 | Campbell |
| 2002/0094701 A1 | 7/2002 | Biegelsen |
| 2002/0113739 A1 | 8/2002 | Howard |
| 2002/0128700 A1 | 9/2002 | Cross, Jr. |
| 2002/0145467 A1 | 10/2002 | Minch |
| 2002/0151934 A1 | 10/2002 | Levine |
| 2002/0158330 A1 | 10/2002 | Moon |
| 2003/0017848 A1 | 1/2003 | Engstrom |
| 2003/0045025 A1 | 3/2003 | Coyle |
| 2003/0090000 A1 | 5/2003 | Caletka |
| 2003/0097165 A1 | 5/2003 | Krulevitch |
| 2003/0120271 A1 | 6/2003 | Burnside |
| 2003/0146017 A1* | 8/2003 | Fan ............. H01L 23/49827 174/138 G |
| 2003/0162507 A1 | 8/2003 | Vatt |
| 2003/0168725 A1 | 9/2003 | Warner |
| 2003/0214408 A1 | 11/2003 | Grajales |
| 2003/0236455 A1 | 12/2003 | Swanson |
| 2004/0006264 A1 | 1/2004 | Mojarradi |
| 2004/0007376 A1 | 1/2004 | Urdahl |
| 2004/0085469 A1 | 5/2004 | Johnson |
| 2004/0092806 A1 | 5/2004 | Sagon |
| 2004/0106334 A1 | 6/2004 | Suzuki |
| 2004/0135094 A1 | 7/2004 | Niigaki |
| 2004/0138558 A1 | 7/2004 | Dunki-Jacobs |
| 2004/0149921 A1 | 8/2004 | Smyk |
| 2004/0178466 A1 | 9/2004 | Merrill |
| 2004/0192082 A1 | 9/2004 | Wagner |
| 2004/0201134 A1 | 10/2004 | Kawai |
| 2004/0203486 A1 | 10/2004 | Shepherd |
| 2004/0221370 A1 | 11/2004 | Hannula |
| 2004/0243204 A1 | 12/2004 | Maghribi |
| 2005/0021103 A1 | 1/2005 | DiLorenzo |
| 2005/0029680 A1 | 2/2005 | Jung |

(56) References Cited

U.S. PATENT DOCUMENTS

| | | |
|---|---|---|
| 2005/0067293 A1 | 3/2005 | Naito |
| 2005/0070778 A1 | 3/2005 | Lackey |
| 2005/0096513 A1 | 5/2005 | Ozguz |
| 2005/0113744 A1 | 5/2005 | Donoghue |
| 2005/0139683 A1 | 6/2005 | Yi |
| 2005/0171524 A1 | 8/2005 | Stern |
| 2005/0203366 A1 | 9/2005 | Donoghue |
| 2005/0248312 A1 | 11/2005 | Cao |
| 2005/0285262 A1 | 12/2005 | Knapp |
| 2006/0003709 A1 | 1/2006 | Wood |
| 2006/0038182 A1 | 2/2006 | Rogers |
| 2006/0071349 A1 | 4/2006 | Tokushige |
| 2006/0084394 A1 | 4/2006 | Engstrom |
| 2006/0106321 A1 | 5/2006 | Lewinsky |
| 2006/0128346 A1 | 6/2006 | Yasui |
| 2006/0154398 A1 | 7/2006 | Qing |
| 2006/0160560 A1 | 7/2006 | Josenhans |
| 2006/0248946 A1 | 11/2006 | Howell |
| 2006/0257945 A1 | 11/2006 | Masters |
| 2006/0264767 A1 | 11/2006 | Shennib |
| 2006/0270135 A1 | 11/2006 | Chrysler |
| 2006/0286785 A1 | 12/2006 | Rogers |
| 2007/0027514 A1 | 2/2007 | Gerber |
| 2007/0031283 A1 | 2/2007 | Davis |
| 2007/0108389 A1 | 5/2007 | Makela |
| 2007/0113399 A1 | 5/2007 | Kumar |
| 2007/0123756 A1 | 5/2007 | Kitajima |
| 2007/0270672 A1 | 11/2007 | Hayter |
| 2008/0036097 A1 | 2/2008 | Ito |
| 2008/0046080 A1 | 2/2008 | Vanden Bulcke |
| 2008/0074383 A1 | 3/2008 | Dean |
| 2008/0096620 A1 | 4/2008 | Lee |
| 2008/0099898 A1 | 5/2008 | Cui |
| 2008/0139894 A1 | 6/2008 | Szydlo-Moore |
| 2008/0157235 A1 | 7/2008 | Rogers |
| 2008/0188912 A1 | 8/2008 | Stone |
| 2008/0193749 A1 | 8/2008 | Thompson |
| 2008/0204021 A1 | 8/2008 | Leussler |
| 2008/0211087 A1 | 9/2008 | Mueller-Hipper |
| 2008/0237840 A1 | 10/2008 | Alcoe |
| 2008/0259576 A1 | 10/2008 | Johnson |
| 2008/0262381 A1 | 10/2008 | Kolen |
| 2008/0287167 A1 | 11/2008 | Caine |
| 2008/0313552 A1 | 12/2008 | Buehler |
| 2009/0000377 A1 | 1/2009 | Shipps |
| 2009/0001550 A1 | 1/2009 | Yonggang |
| 2009/0015560 A1 | 1/2009 | Robinson |
| 2009/0017884 A1 | 1/2009 | Rotschild |
| 2009/0048556 A1 | 2/2009 | Durand |
| 2009/0088750 A1 | 4/2009 | Hushka |
| 2009/0107704 A1 | 4/2009 | Vanfleteren |
| 2009/0154736 A1 | 6/2009 | Lee |
| 2009/0178274 A1 | 7/2009 | Kumar |
| 2009/0184254 A1 | 7/2009 | Miura |
| 2009/0204168 A1 | 8/2009 | Kallmeyer |
| 2009/0215385 A1 | 8/2009 | Waters |
| 2009/0225751 A1 | 9/2009 | Koenck |
| 2009/0261828 A1 | 10/2009 | Nordmeyer-Massner |
| 2009/0273909 A1 | 11/2009 | Shin |
| 2009/0283891 A1* | 11/2009 | Dekker ............... H01L 23/5387 257/690 |
| 2009/0291508 A1 | 11/2009 | Babu |
| 2009/0294803 A1 | 12/2009 | Nuzzo |
| 2009/0322480 A1 | 12/2009 | Benedict |
| 2010/0002402 A1 | 1/2010 | Rogers |
| 2010/0059863 A1 | 3/2010 | Rogers |
| 2010/0072577 A1 | 3/2010 | Nuzzo |
| 2010/0073669 A1 | 3/2010 | Colvin |
| 2010/0087782 A1 | 4/2010 | Ghaffari |
| 2010/0090781 A1 | 4/2010 | Yamamoto |
| 2010/0090824 A1 | 4/2010 | Rowell |
| 2010/0116526 A1 | 5/2010 | Arora |
| 2010/0117660 A1 | 5/2010 | Douglas |
| 2010/0178722 A1 | 7/2010 | De Graff |
| 2010/0207265 A1 | 8/2010 | Muthukumar |
| 2010/0245011 A1 | 9/2010 | Chatzopoulos |
| 2010/0271191 A1 | 10/2010 | De Graff |
| 2010/0298895 A1 | 11/2010 | Ghaffari |
| 2010/0317132 A1 | 12/2010 | Rogers |
| 2010/0321161 A1 | 12/2010 | Isabell |
| 2010/0327387 A1 | 12/2010 | Kasai |
| 2011/0011179 A1 | 1/2011 | Gustafsson |
| 2011/0034912 A1 | 2/2011 | De Graff |
| 2011/0051384 A1 | 3/2011 | Kriechbaum |
| 2011/0054583 A1 | 3/2011 | Litt |
| 2011/0098583 A1 | 4/2011 | Pandia |
| 2011/0101789 A1 | 5/2011 | Salter |
| 2011/0121822 A1 | 5/2011 | Parsche |
| 2011/0140897 A1 | 6/2011 | Purks |
| 2011/0175735 A1 | 7/2011 | Forster |
| 2011/0184320 A1 | 7/2011 | Shipps |
| 2011/0215931 A1 | 9/2011 | Callsen |
| 2011/0218756 A1 | 9/2011 | Callsen |
| 2011/0218757 A1 | 9/2011 | Callsen |
| 2011/0220890 A1 | 9/2011 | Nuzzo |
| 2011/0263950 A1 | 10/2011 | Larson |
| 2011/0277813 A1 | 11/2011 | Rogers |
| 2011/0284268 A1 | 11/2011 | Palaniswamy |
| 2011/0306851 A1 | 12/2011 | Wang |
| 2012/0016258 A1 | 1/2012 | Webster |
| 2012/0051005 A1 | 3/2012 | Vanfleteren |
| 2012/0052268 A1 | 3/2012 | Axisa |
| 2012/0065937 A1 | 3/2012 | De Graff |
| 2012/0074546 A1 | 3/2012 | Chong |
| 2012/0087216 A1 | 4/2012 | Keung |
| 2012/0091594 A1 | 4/2012 | Landesberger |
| 2012/0092178 A1 | 4/2012 | Callsen |
| 2012/0092222 A1 | 4/2012 | Kato |
| 2012/0101413 A1 | 4/2012 | Beetel |
| 2012/0101538 A1 | 4/2012 | Ballakur |
| 2012/0108012 A1 | 5/2012 | Yasuda |
| 2012/0126418 A1 | 5/2012 | Feng |
| 2012/0157804 A1 | 6/2012 | Rogers |
| 2012/0172697 A1 | 7/2012 | Urman |
| 2012/0178367 A1 | 7/2012 | Matsumoto |
| 2012/0226130 A1 | 9/2012 | De Graff |
| 2012/0244848 A1 | 9/2012 | Ghaffari |
| 2012/0256308 A1 | 10/2012 | Helin |
| 2012/0316455 A1 | 12/2012 | Rahman |
| 2012/0327608 A1 | 12/2012 | Rogers |
| 2013/0041235 A1 | 2/2013 | Rogers |
| 2013/0099358 A1 | 4/2013 | Elolampi |
| 2013/0100618 A1 | 4/2013 | Rogers |
| 2013/0116520 A1 | 5/2013 | Roham |
| 2013/0118255 A1 | 5/2013 | Callsen |
| 2013/0150693 A1 | 6/2013 | D'angelo |
| 2013/0185003 A1 | 7/2013 | Carbeck |
| 2013/0192356 A1 | 8/2013 | De Graff |
| 2013/0200268 A1 | 8/2013 | Rafferty |
| 2013/0211761 A1 | 8/2013 | Brandsma |
| 2013/0214300 A1 | 8/2013 | Lerman |
| 2013/0215467 A1 | 8/2013 | Fein |
| 2013/0225965 A1 | 8/2013 | Ghaffari |
| 2013/0237150 A1 | 9/2013 | Royston |
| 2013/0245388 A1 | 9/2013 | Rafferty |
| 2013/0274562 A1 | 10/2013 | Ghaffari |
| 2013/0313713 A1 | 11/2013 | Arora |
| 2013/0316442 A1 | 11/2013 | Meurville |
| 2013/0316487 A1 | 11/2013 | De Graff |
| 2013/0316645 A1 | 11/2013 | Li |
| 2013/0320503 A1 | 12/2013 | Nuzzo |
| 2013/0321373 A1 | 12/2013 | Yoshizumi |
| 2013/0328219 A1 | 12/2013 | Chau |
| 2014/0001058 A1 | 1/2014 | Ghaffari |
| 2014/0012160 A1 | 1/2014 | Ghaffari |
| 2014/0012242 A1 | 1/2014 | Lee |
| 2014/0022746 A1 | 1/2014 | Hsu |
| 2014/0039290 A1 | 2/2014 | De Graff |
| 2014/0097944 A1 | 4/2014 | Fastert |
| 2014/0110859 A1 | 4/2014 | Rafferty |
| 2014/0140020 A1 | 5/2014 | Rogers |
| 2014/0188426 A1 | 7/2014 | Fastert |
| 2014/0191236 A1 | 7/2014 | Nuzzo |
| 2014/0216524 A1 | 8/2014 | Rogers |

(56) References Cited

U.S. PATENT DOCUMENTS

| | | |
|---|---|---|
| 2014/0240932 A1 | 8/2014 | Hsu |
| 2014/0249520 A1 | 9/2014 | Ghaffari |
| 2014/0303452 A1 | 10/2014 | Ghaffari |
| 2014/0303680 A1 | 10/2014 | Donnelly |
| 2014/0340857 A1 | 11/2014 | Hsu |
| 2014/0374872 A1 | 12/2014 | Rogers |
| 2014/0375465 A1 | 12/2014 | Fenuccio |
| 2015/0001462 A1 | 1/2015 | Rogers |
| 2015/0019135 A1 | 1/2015 | Kacyvenski |
| 2015/0025394 A1 | 1/2015 | Hong |
| 2015/0035680 A1 | 2/2015 | Li |
| 2015/0069617 A1 | 3/2015 | Arora |
| 2015/0099976 A1 | 4/2015 | Ghaffari |
| 2015/0100135 A1 | 4/2015 | Ives |
| 2015/0194817 A1 | 7/2015 | Lee |
| 2015/0237711 A1 | 8/2015 | Rogers |
| 2015/0241288 A1 | 8/2015 | Keen |
| 2015/0260713 A1 | 9/2015 | Ghaffari |
| 2015/0272652 A1 | 10/2015 | Ghaffari |
| 2015/0286913 A1 | 10/2015 | Fastert |
| 2015/0320472 A1 | 11/2015 | Ghaffari |
| 2015/0335254 A1 | 11/2015 | Elolampi |
| 2015/0342036 A1 | 11/2015 | Fastert |
| 2016/0027834 A1 | 1/2016 | de Graff |
| 2016/0035658 A1* | 2/2016 | Kessler ............... H01L 23/3735 361/688 |
| 2016/0045162 A1 | 2/2016 | De Graff |
| 2016/0081192 A1 | 3/2016 | Hsu |
| 2016/0086909 A1 | 3/2016 | Garlock |
| 2016/0095652 A1 | 4/2016 | Lee |
| 2016/0099214 A1 | 4/2016 | Dalal |
| 2016/0099227 A1 | 4/2016 | Dalal |
| 2016/0111353 A1 | 4/2016 | Rafferty |
| 2016/0135740 A1 | 5/2016 | Ghaffari |
| 2016/0213262 A1 | 7/2016 | Ghaffari |
| 2016/0213424 A1 | 7/2016 | Ghaffari |
| 2016/0228640 A1 | 8/2016 | Pindado |
| 2016/0232807 A1 | 8/2016 | Ghaffari |
| 2016/0240061 A1 | 8/2016 | Li |
| 2016/0249174 A1 | 8/2016 | Patel |
| 2016/0256070 A1 | 9/2016 | Murphy |
| 2017/0086291 A1* | 3/2017 | Cotton ............... H01L 23/5387 |
| 2019/0087622 A1* | 3/2019 | Benkley, III ....... G06K 9/00006 |

FOREIGN PATENT DOCUMENTS

| | | |
|---|---|---|
| EP | 1808124 A2 | 7/2007 |
| EP | 2259062 A2 | 12/2010 |
| JP | 05-087511 A | 4/1993 |
| JP | 2005-052212 A | 3/2005 |
| JP | 2009-170173 A | 7/2009 |
| WO | WO 1999/038211 A2 | 7/1999 |
| WO | WO 2005/122285 A2 | 12/2005 |
| WO | WO 2003/021679 A2 | 3/2006 |
| WO | WO 2007/003019 A2 | 1/2007 |
| WO | WO 2007/024983 A2 | 3/2007 |
| WO | WO 2007/116344 A1 | 10/2007 |
| WO | WO 2007/136726 A2 | 11/2007 |
| WO | WO 2008/030960 A2 | 3/2008 |
| WO | WO 2009/111641 A1 | 9/2009 |
| WO | WO 2009/114689 A1 | 9/2009 |
| WO | WO 2010/036807 A1 | 4/2010 |
| WO | WO 2010/042653 A1 | 4/2010 |
| WO | WO 2010/042957 A2 | 4/2010 |
| WO | WO 2010/046883 A1 | 4/2010 |
| WO | WO 2010/056857 A2 | 5/2010 |
| WO | WO 2010/081137 A2 | 7/2010 |
| WO | WO 2010/082993 A2 | 7/2010 |
| WO | WO 2010/102310 A2 | 9/2010 |
| WO | WO 2010/132552 A1 | 11/2010 |
| WO | WO 2011/003181 A1 | 1/2011 |
| WO | WO 2011/041727 A1 | 4/2011 |
| WO | WO 2011/084450 A1 | 7/2011 |
| WO | WO 2011/084709 A2 | 7/2011 |
| WO | WO 2011/127331 A2 | 10/2011 |
| WO | WO 2012/125494 A2 | 9/2012 |
| WO | WO 2012/166686 A2 | 12/2012 |
| WO | WO 2013/010171 A1 | 1/2013 |
| WO | WO 2013/022853 A1 | 2/2013 |
| WO | WO 2013/033724 A1 | 3/2013 |
| WO | WO 2013/034987 A3 | 3/2013 |
| WO | WO 2013/049716 A1 | 4/2013 |
| WO | WO 2013/052919 A2 | 4/2013 |
| WO | WO 2013/170032 A2 | 11/2013 |
| WO | WO 2014/007871 A1 | 1/2014 |
| WO | WO 2014/058473 A1 | 4/2014 |
| WO | WO 2014/059032 A1 | 4/2014 |
| WO | WO 2014/106041 A1 | 7/2014 |
| WO | WO 2014/110176 A1 | 7/2014 |
| WO | WO 2014/130928 A2 | 8/2014 |
| WO | WO 2014/130931 A1 | 8/2014 |
| WO | WO 2014/186467 A2 | 11/2014 |
| WO | WO 2014/197443 A1 | 12/2014 |
| WO | WO 2014/205434 A2 | 12/2014 |
| WO | WO 2015/021039 A1 | 2/2015 |
| WO | WO 2015/054312 A1 | 4/2015 |
| WO | WO 2015/077559 A1 | 5/2015 |
| WO | WO 2015/080991 A1 | 6/2015 |
| WO | WO 2015/102951 A2 | 7/2015 |
| WO | WO 2015/103483 A1 | 7/2015 |
| WO | WO 2015/103580 A2 | 7/2015 |
| WO | WO 2015/127458 A1 | 8/2015 |
| WO | WO 2015/134588 A1 | 9/2015 |
| WO | WO 2015/138712 A1 | 9/2015 |
| WO | WO 2016/048888 A1 | 3/2016 |
| WO | WO 2016/054512 A1 | 4/2016 |
| WO | WO 2016/057318 A1 | 4/2016 |
| WO | WO 2016/081244 A1 | 5/2016 |
| WO | WO 2016/127050 A1 | 8/2016 |
| WO | WO 2016/134306 A1 | 8/2016 |

OTHER PUBLICATIONS

Written Opinion dated Dec. 9, 2016 which issued in International Patent Application No. PCT/US2016/041927 (9 pages).

Carvalhal et al., "Electrochemical Detection in a Paper-Based Separation Device", Analytical Chemistry, vol. 82, No. 3, (1162-1165) (4 pages) (Jan. 7, 2010).

Demura et al "Immobilization of Glucose Oxidase with *Bombyx Mori* Silk Fibroin by Only Stretching Treatment and its Application to Glucose Sensor," Biotechnology and Bioengineering, vol. 33, 598-603 (6 pages) (1989).

Ellerbee et al., "Quantifying Colorimetric Assays in Paper-Based Microfluidic Devices by Measuring the Transmission of Light through Paper," Analytical Chemistry, vol. 81, No. 20 8447-8452, (6 pages) (Oct. 15, 2009).

Halsted, "Ligature and Suture Material," Journal of the American Medical Association, vol. LX, No. 15, 1119-1126, (8 pages) (Apr. 12, 1913).

Kim et al., "Complementary Metal Oxide Silicon Integrated Circuits Incorporating Monolithically Integrated Stretchable Wavy Interconnects," Applied Physics Letters, vol. 93, 044102-044102.3 (3 pages) (Jul. 31, 2008).

Kim et al., "Dissolvable Films of Silk Fibroin for Ultrathin Conformal Bio-Integrated Electronics," Nature, 1-8 (8 pages) (Apr. 18, 2010).

Kim et al., "Materials and Noncoplanar Mesh Designs for Integrated Circuits with Linear Elastic Responses to Extreme Mechanical Deformations," PNAS, vol. 105, No. 48, 18675-18680 (6 pages) (Dec. 2, 2008).

Kim et al., "Stretchable and Foldable Silicon Integrated Circuits," Science, vol. 320, 507-511 (5 pages) (Apr. 25, 2008).

Kim et al., "Electrowetting on Paper for Electronic Paper Display," ACS Applied Materials & Interfaces, vol. 2, No. 11, (3318-3323) (6 pages) (Nov. 24, 2010).

Ko et al., "A Hemispherical Electronic Eye Camera Based on Compressible Silicon Optoelectronics," Nature, vol. 454, 748-753 (6 pages) (Aug. 7, 2008).

(56) References Cited

OTHER PUBLICATIONS

Lawrence et al., "Bioactive Silk Protein Biomaterial Systems for Optical Devices," Biomacromolecules, vol. 9, 1214-1220 (7 pages) (Nov. 4, 2008).
Meitl et al., "Transfer Printing by Kinetic Control of Adhesion to an Elastomeric Stamp," Nature, vol. 5, 33-38 (6 pages) (Jan. 2006).
Omenetto et al., "A New Route for Silk," Nature Photonics, vol. 2, 641-643 (3 pages) (Nov. 2008).
Omenetto et al., "New Opportunities for an Ancient Material," Science, vol. 329, 528-531 (5 pages) (Jul. 30, 2010).
Siegel et al., "Foldable Printed Circuit Boards on Paper Substrates," Advanced Functional Materials, vol. 20, No. 1, 28-35, (8 pages) (Jan. 8, 2010).
Tsukada et al., "Structural Changes of Silk Fibroin Membranes Induced by Immersion in Methanol Aqueous Solutions," Journal of Polymer Science, vol. 32, 961-968 (8 pages) (1994).
Wang et al., "Controlled Release From Multilayer Silk Biomaterial Coatings to Modulate Vascular Cell Responses" Biomaterials, 29, 894-903 (10 pages) (Nov. 28, 2008).
Wikipedia, "Ball bonding" article [online]. Cited in PCT/US2015/051210 search report dated Mar. 1, 2016 with the following information "Jun. 15, 2011 [retrieved on Nov. 15, 2015}. Retrieved Dec. 29, 2018 from the Internet: <URL: https://web.archive.org/web/20110615221003/hltp://en.wikipedia.org/wiki/Ball_bonding>., entire document, especially para 1, 4, 5, 6," 2 pages, last page says ("last modified on May 11, 2011").

\* cited by examiner

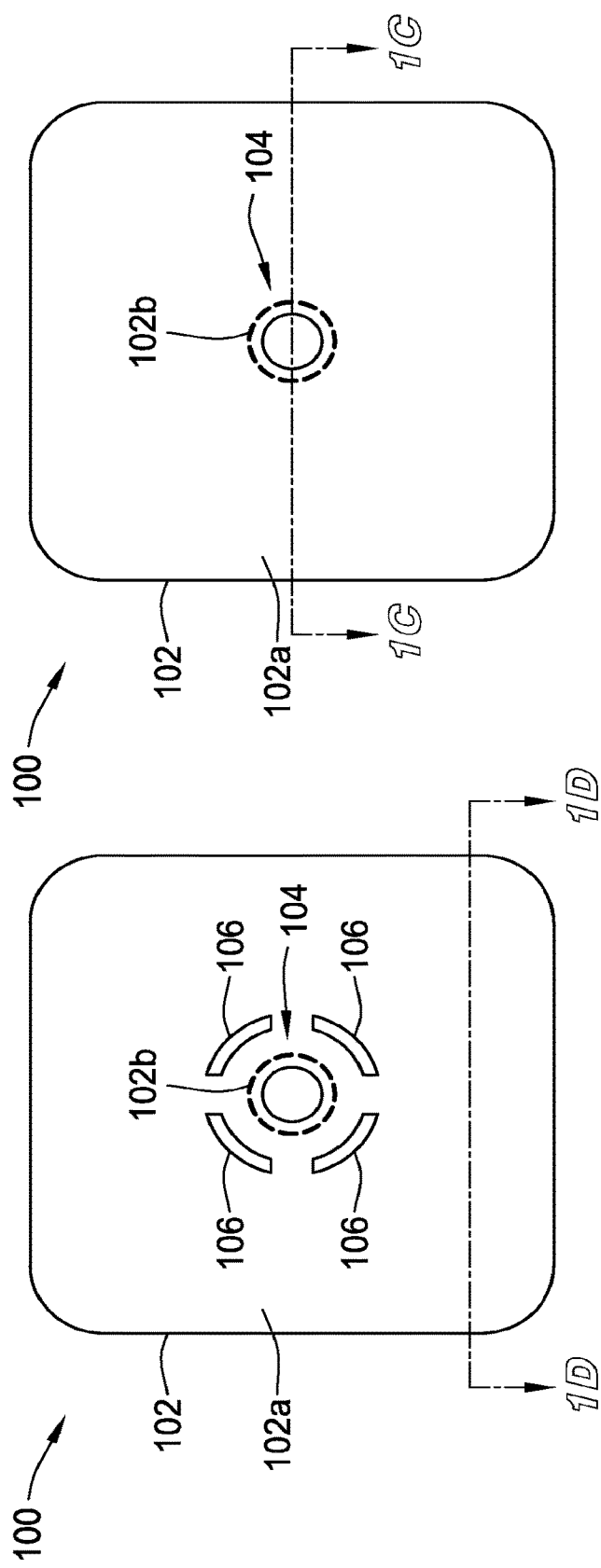
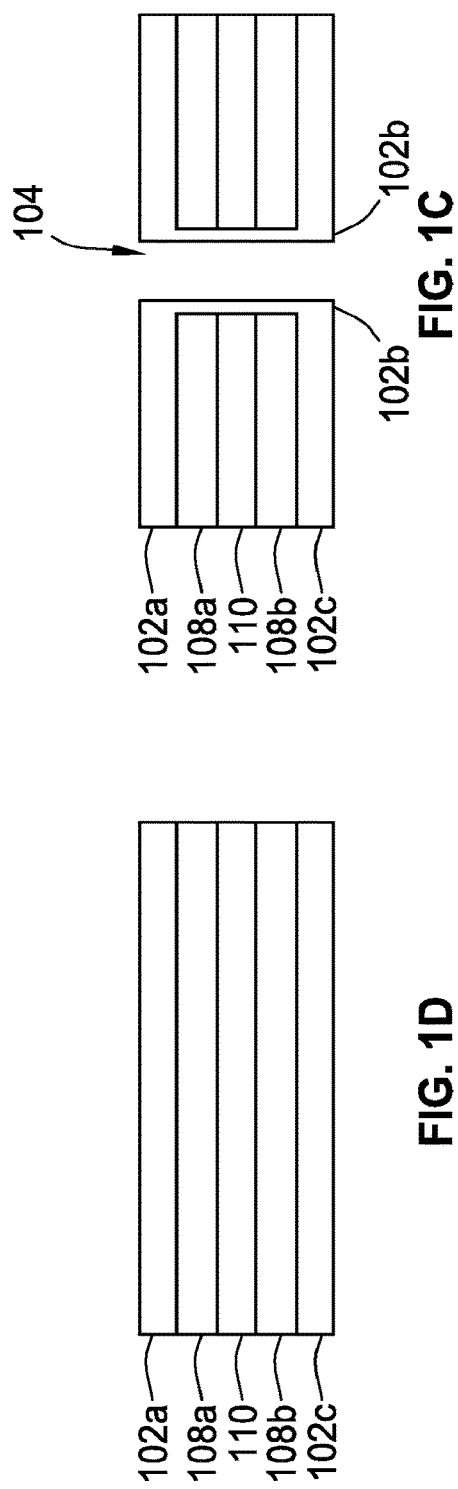
FIG. 1B
FIG. 1C
FIG. 1A
FIG. 1D

CONDUCTIVE STIFFENER, METHOD OF MAKING A CONDUCTIVE STIFFENER, AND CONDUCTIVE ADHESIVE AND ENCAPSULATION LAYERS

CROSS-REFERENCE TO RELATED APPLICATION

This application claims the benefit of and priority to U.S. Application No. 62/194,058, filed Jul. 17, 2015, and entitled, "CONDUCTIVE STIFFENER, METHOD OF MAKING A CONDUCTIVE STIFFENER, AND CONDUCTIVE ADHESIVE AND ENCAPSULATION LAYERS," which is hereby incorporated by reference herein in its entirety.

TECHNICAL FIELD

The present disclosure relates generally to sensors. More particularly, aspects of this disclosure relate to sensors wearable on a body, such as a human body.

BACKGROUND

Integrated circuits are the cornerstone of the information age and the foundation of today's information technology industries. The integrated circuit, a.k.a. "IC," "chip," or "microchip," is a set of interconnected electronic components, such as transistors, capacitors, and resistors, which are etched or imprinted onto a semiconducting material, such as silicon or germanium. Integrated circuits take on various forms including, as some non-limiting examples, microprocessors, amplifiers, Flash memories, application specific integrated circuits (ASICs), static random access memories (SRAMs), digital signal processors (DSPs), dynamic random access memories (DRAMs), erasable programmable read only memories (EPROMs), and programmable logic. Integrated circuits are used in innumerable products, including computers (e.g., personal, laptop, and tablet computers), smartphones, flat-screen televisions, medical instruments, telecommunication and networking equipment, airplanes, watercraft, and automobiles.

Advances in integrated circuit technology and microchip manufacturing have led to a steady decrease in chip size and an increase in circuit density and circuit performance. The scale of semiconductor integration has advanced to the point where a single semiconductor chip can hold tens of millions to over a billion devices in a space smaller than a U.S. penny. Moreover, the width of each conducting line in a modern microchip can be made as small as a fraction of a nanometer. The operating speed and overall performance of a semiconductor chip (e.g., clock speed and signal net switching speeds) has concomitantly increased with the level of integration. To keep pace with increases in on-chip circuit switching frequency and circuit density, semiconductor packages currently offer higher pin counts, greater power dissipation, more protection, and higher speeds than packages of just a few years ago.

The advances in integrated circuits have led to related advances within other fields. One such field is sensors. Advances in integrated circuits have allowed sensors to become smaller and more efficient, while simultaneously becoming more capable of performing complex operations. Other advances in the field of sensors and circuitry in general have led to wearable circuitry, a.k.a. "wearable devices" or "wearable systems." Within the medical field, as an example, wearable devices have given rise to new methods of acquiring, analyzing, and diagnosing medical issues with patients, by having the patient wear a sensor that monitors specific characteristics. Related to the medical field, other wearable devices have been created within the sports and recreational fields for the purpose of monitoring physical activity and fitness. For example, a user may don a wearable device, such as a wearable running coach, to measure the distance traveled during an activity (e.g., running, walking, etc.), and measure the kinematics of the user's motion during the activity.

An important aspect of a wearable device is the interface between the wearable device and the biological surface of the user, such as the user's skin, and the ability of the wearable device to measure the specific characteristics of the user. Many of the specific characteristics measured by the wearable device rely on the wearable device being able to detect biological signals from the user, such as thermal and/or electrical signals. Conventionally, the wearable devices had to rely on connecting to external electrodes to measure the biological signals. However, such external electrodes that connect to such skin-mounted wearable devices are typically cumbersome and add to the overall thickness of the wearable devices. Consequently, the additional thickness of the external electrodes restricts the ability of the wearable device to conform, and can contribute to user discomfort.

Further, the wearable device must be robust and be able to withstand a wide variety of movements and environments during use to be effective both functionally and economically. However, modifications to the wearable device to increase its durability cannot impact the functionality of the device, such as the ability of the wearable device to detect the biological signals of the user. Additionally, while the wearable devices are generally conformable, certain portions of the wearable devices may need reinforcement, such as to protect electronic components. Again, such reinforcement cannot impact the ability of the wearable device to function, such as detecting biological signals of the user.

Accordingly, a need exists for a wearable device with reinforcements to electrical components that do not affect the ability of the wearable device to function as intended. A need also exists, therefore, for wearable devices that are protected from the external environment, while not impacting the ability of the devices to conform to biological surfaces.

SUMMARY

Aspects of the present invention include a device having a flexible printed circuit board (FPCB) and one or more conductive stiffeners. The flexible printed circuit board assembly includes a plurality of discrete operative electrically interconnected electronic components attached to the flexible printed circuit board. One or more of the discrete electronic components can be soldered to conductive contact pads on the flexible printed circuit board. The conductive pads can be connected to circuit traces that interconnect the electronic components. One or more stiffeners can be affixed to the backside of the flexible printed circuit board to limit the ability of the flexible printed circuit board to flex and reduce the risk of the solder joints breaking when the FPCB is flexed. Each stiffener can be electrically conductive (e.g., to function as an electrode) and can be electrically connected to conductive contact pads on the backside of flexible printed circuit board. Printed circuit board traces can connect the conductive contact pad to one or more electronic components attached to the flexible printed circuit board.

Additional aspects of the present disclosure include a conductive stiffener. The conductive stiffener can include one or more non-conductive substrate layers, one or more holes through the non-conductive substrate, and a conductive material attached (e.g., laminated or plated) to a surface of the non-conductive substrate. One or more of the holes can include a conductive material or conductive layer as well. The layer of conductive material on the non-conductive substrate can be electrically connected to the conductive material in one or more of the holes.

Further aspects of the present disclosure include a method of forming a conductive stiffener. Aspects of the method include adhering at least two non-conductive substrate sheets together with an adhesive to form a stiffener, forming a hole through the stiffener, and forming a layer of conductive material on one or more surfaces of the stiffener. The conductive material can be formed within the hole in order to electrically connect the conductive material formed on opposite surfaces (e.g., the top and bottom surfaces) of the stiffener. The method can further include forming a resist layer (e.g., a photoresist layer) on the pad of conductive material on a top surface of the stiffener according to a thermal relief pattern surrounding the hole. Further, the method can include removing conductive material exposed through the resist layer to form the thermal relief pattern in the conductive material on the surface of the stiffener.

Still further aspects of the present concepts include a method of attaching a stiffener to a flexible printed circuit board assembly. Aspects of the method include adhering the non-conductive substrate sheets together with an adhesive to form a stiffener, forming a hole through the stiffener, and forming a layer of conductive material on the stiffener. The conductive material can be formed within the hole in order to electrically connect the conductive material formed on opposite surfaces of the stiffener. Aspects of the method can also include forming a resist layer on the pad of conductive material on a top surface of the stiffener according to a thermal relief pattern surrounding the hole, removing conductive material exposed through the resist layer to form the thermal relief pattern in the pad of conductive material on the top surface, and applying an adhesive to the top surface of the stiffener to adhere the top surface of the stiffener to the bottom of the flexible printed circuit board assembly. Still further aspects of the method include adhering the top surface of the stiffener to a bottom surface of the flexible printed circuit board assembly with the hole aligned with a conductive contact pad on the bottom surface of the flexible printed circuit board assembly, and filling the hole with solder or another conductor to electrically and/or thermally connect one or more conductive surfaces of the stiffener to the flexible printed circuit board assembly.

The above summary is not intended to represent each embodiment or every aspect of the present disclosure. Rather, the foregoing summary merely provides an exemplification of some of the novel aspects and features set forth herein. The above features and advantages, and other features and advantages of the present disclosure, will be readily apparent from the following detailed description of representative embodiments and modes for carrying out the present invention when taken in connection with the accompanying drawings and the appended claims.

BRIEF DESCRIPTION OF THE DRAWINGS

The disclosure will be better understood from the following description of exemplary embodiments together with reference to the accompanying drawings, in which:

FIG. 1A shows a top view of a conductive stiffener, in accord with aspects of the present concepts;

FIG. 1B shows a bottom view of a conductive stiffener, in accord with aspects of the present concepts;

FIGS. 1C and 1D show several cross-section views of a conductive stiffener, in accord with aspects of the present concepts;

Figure 3:
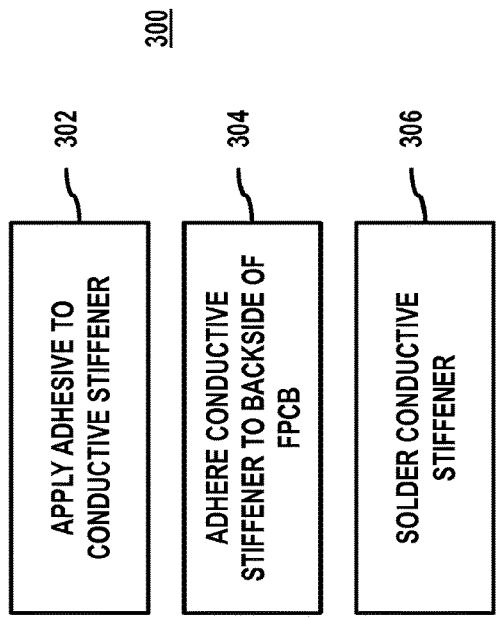
FIG. 3 shows a flow diagram of a process for attaching the conductive stiffener to a flexible printed circuit board (FPCB), in accord with aspects of the present concepts.

The present disclosure is susceptible to various modifications and alternative forms, and some representative embodiments have been shown by way of example in the drawings and will be described in detail herein. It should be understood, however, that the invention is not intended to be limited to the particular forms disclosed. Rather, the disclosure is to cover all modifications, equivalents, and alternatives falling within the spirit and scope of the invention as defined by the appended claims.

DETAILED DESCRIPTION OF THE ILLUSTRATED EMBODIMENTS

This disclosure is susceptible of embodiment in many different forms. There are shown in the drawings, and will herein be described in detail, representative embodiments with the understanding that the present disclosure is to be considered as an exemplification of the principles of the present disclosure and is not intended to limit the broad aspects of the disclosure to the embodiments illustrated. To that extent, elements and limitations that are disclosed, for example, in the Abstract, Summary, and Detailed Description sections, but not explicitly set forth in the claims, should not be incorporated into the claims, singly or collectively, by implication, inference, or otherwise. For purposes of the present detailed description, unless specifically disclaimed: the singular includes the plural and vice versa; and the word "including" means "including without limitation." Moreover, words of approximation, such as "about," "almost," "substantially," "approximately," and the like, can be used herein in the sense of "at, near, or nearly at," or "within 3-5% of," or "within acceptable manufacturing tolerances," or any logical combination thereof, for example.

For purposes of illustration and to facilitate an understanding of the invention, the illustrative embodiments are described making reference to "top" and "bottom" in accordance with how the features are shown in the drawings. These reference designations are provided for convenience and the invention can be implemented with the features in other orientations, for example, with the positions reversed and device up-side down.

Flexible printed circuit board (FPCB) manufacturers typically use stiffeners on the backside (e.g., the side without components) or the component side of the FPCB assembly for both ease of assembly and reliability purposes. The stiffeners can be used to reinforce the FPCB assembly in the areas where electronic components are soldered to the FPCB to limit flexing that can cause the solder joints to break reducing the reliability of the assembly. According to the aspects of the present disclosure, the stiffeners can be conductive stiffeners and utilized to transmit thermal and/or electrical energy to components of the FPCB, rather than requiring externally attached electrodes. In accordance with some embodiments of the invention, the conductive stiffeners can function as electrodes for thermal and/or electrical measurements on a biological surface (e.g., tissue, such as skin) and provide mechanical stiffening of the FPCB assembly that can be incorporated into a conformable wearable device. Such conductive stiffeners can reduce the overall complexity and form factor of wearable devices by providing integrated permanent electrodes. The slender form factor of the wearable device can be achieved by fabricating and integrating positive, negative, and/or reference electrodes directly on the body-contacting surface of the FPCB assembly or the wearable device. The resulting conductive stiffener can be used to conduct electrical and/or thermal energy from biological tissue (e.g., skin, soft tissue, organs, etc.) to components mounted to the FPCB. The resulting conductive stiffener can also be used to increase the stiffness of at least a portion of the FPCB assembly. According to some embodiments, therefore, the conductive stiffener can have the same or similar shape and general dimensions as the FPCB assembly or a portion thereof.

The conductive stiffeners can be adhered and electrically and/or thermally connected to the surface (e.g., the backside or the component side) of the FPCB to allow for the collection of bio-potentials and/or bio-impedances such as electrooculography (EOG), electroencephalography (EEG), electromyogram (EMG), galvanic skin response (GSR), and electrocardiogram (ECG) signals by components of the FPCB assembly that forms part of the wearable device. The conductive stiffeners can also allow for the collection of temperature data through a thermally conductive medium and the ability to measure skin, body and/or tissue temperature without the need for auxiliary electrodes. The conductive stiffeners can also allow for the collection of bio-impedance data through the conductive skin contacting surfaces of the conductive stiffeners without the need for auxiliary electrodes.

FIGS. 1A-1D show various diagrammatic views of a conductive stiffener 100, in accord with aspects of the invention. Specifically, FIG. 1A shows a top view of the conductive stiffener 100. The dimensions (e.g., length and width) of the conductive stiffener 100 can correspond to the dimensions of the FPCB (or a portion thereof) to be stiffened. The conductive stiffener 100 can be covered with a conductive material 102 such that the top of the conductive stiffener 100 has top conductive layer 102a. According to some embodiments, the conductive material 102 can be any conductive material, such as any conducting metal. By way of example, and without limitation, the conductive material 102 can include copper, gold, silver, nickel, chrome, brass, bronze, lead free hot air solder, electroless nickel, immersion palladium, electroless palladium, immersion gold, electroless gold, electrolytic nickel, electrolytic gold, immersion tin, immersion silver, and various metal alloys. According to some embodiments, the conductive material 102 can be a ferrous material, such as stainless steel. According to the conductive material 102 being a ferrous material, the conductive stiffener 100 could also function as an alignment mechanism for applications associated with magnets. By way of example, and without limitation, the conductive stiffener 100 could function as an alignment mechanism for a wireless charger used in conjunction with the FPCB assembly.

The conductive stiffener 100 can also include one or more vertical interconnect access holes or VIAs 104 that extend through the conductive stiffener 100 to electrically and/or thermally connect the top conductive layer 102a with bottom conductive layer 102c. Although shown as being in the center of the conductive stiffener 100, the VIA(s) 104 can be located at other locations in the stiffener and can be positioned to align with conductive contact pads of the FPCB. The VIA 104 can be lined or filled with conductive material 102 forming a conductive tube or hollow column 102b, such as by plating or filling. In accordance with some embodiments, the VIA 104 can be surrounded by thermal reliefs 106, which are areas in the surface of the conductive stiffener 100 that do not include the conductive material 102. The thermal reliefs 106 aid in soldering the conductive stiffener 100 to a FPCB assembly.

FIG. 1B shows the bottom of the conductive stiffener 100, in accord with aspects of the present invention. Like the top, the bottom can be covered with the conductive material 102 to form a bottom conductive layer 102c. The bottom of the conductive stiffener 100 does not include the thermal reliefs 106, as shown; however, according to some embodiments, the bottom may also include thermal reliefs 106 depending on the intended placement of the conductive stiffener 100.

Referring to FIGS. 1C and 1D, FIG. 1C shows a cross-section view of the conductive stiffener 100 through the line 1C-1C in FIG. 1B, and FIG. 1D shows a cross-section view of the conductive stiffener 100 through line 1D-1D in FIG. 1A. As shown, the conductive stiffener 100 can include a top conductive layer 102a and a bottom conductive layer 102c. The conductive stiffener 100 can also include one or more conductive VIAs 104 that electrically and/or thermally connect the bottom conductive layer 102c to the top conductive layer 102a. The conductive stiffener 100 can include one or more non-conductive substrate layers 108a, 108b, between the top conductive layer 102a and bottom conductive layer 102c. The non-conductive substrate layers can be formed from a fiber reinforced material, such as, epoxy fiberglass (e.g., 370HR FR4 epoxy fiberglass sheet) or a FPCB non-conductive base material such as polyester, polyethylene terephthalate (PET), polyimide (PI), polyethylene napthalate (PEN), polyetherimide (PEI), fluropolymers (FEP) or a combination thereof.

As shown in FIGS. 1C and 1D, the conductive stiffener 100 can include one or more top non-conductive substrate layers 108a bonded or adhered to one or more bottom non-conductive substrate layers 108b. One or more adhesive layers 110 can be used to bond or adhere the adjacent non-conductive substrate layers 108a, 108b together.

In accordance with some embodiments, the top non-conductive substrate layer 108a and the bottom reinforced layer 108b can be formed of any type of non-conductive substrate material, such as any material used in the manufacture of a printed circuit board (PCB). According to some embodiments, the top non-conductive substrate layer 108a and the bottom non-conductive substrate layer 108b are formed of 370HR FR-4 glass-reinforced epoxy laminate sheets. However, the top non-conductive substrate layer 108a and the bottom non-conductive substrate layer 108b can be formed of other types of materials used in the PCB arts without departing from the spirit and scope of the present invention.

The adhesive layer 110 can be any suitable adhesive for adhering the top non-conductive substrate layer 108a and the bottom reinforced layer 108b together. According to some embodiments, the adhesive layer 110 can be, for example, an acrylic-based adhesive, such as a Pyralux® FRO200 and FRO300 adhesive, a polyester based adhesive, an epoxy based adhesive, or a polyimide based adhesive. However, the adhesive layer 110 can be formed of other types of adhesives used in the PCB arts without departing from the spirit and scope of the present disclosure.

While reference is made to top and bottom layers throughout the description for purposes illustrating the described examples of the embodiments of the invention, the conductive stiffener can be oriented and used in configurations where the top layer is below the bottom layer as well as in any angular orientation without departing from the scope and spirit of the invention.

According to some embodiments, the top conductive layer 102a and the bottom conductive layer 102b can be formed to a thickness of 0.0014", the top non-conductive substrate layer 108a and the bottom non-conductive substrate layer 108b can formed to a thickness of 0.002", and the adhesive layer 110 can be formed to a thickness of 0.002". However, the layers can have varying and different thicknesses than the thicknesses disclosed herein without departing from the spirit and scope of the present disclosure. According to some embodiments, reducing the thickness of the various layers reduces the overall thickness of the FPCB assembly as well as the effectiveness as a stiffening component. In accordance with some embodiments, the stiffness can be increased by laminating two or more thin layers of non-conductive substrate material using an appropriate adhesive. Moreover, the thickness of the various layers can be selected such that the conductive stiffener 100 provides both thermal and electrical conductivity between the top conductive layer 102a and the bottom conductive layer 102c while minimizing the overall profile (e.g., thickness) of the conductive stiffener 100 and providing the desired amount stiffness to limit flexing of the attached PFCB.

Although illustrated a described above as including the top non-conductive substrate layer 108a, the adhesive layer 110, and the bottom non-conductive substrate layer 108b, the structure of the conductive stiffener 100 can vary without departing from the spirit and scope of the present disclosure. By way of example, and without limitation, according to some embodiments, the conductive stiffener 100 may instead include a single non-conductive substrate layer between the top conductive layer 102a and the bottom conductive layer 102c. The single non-conductive substrate layer can have the same thickness as, for example, the combination of the top non-conductive substrate layer 108a, the adhesive layer 110, and the bottom non-conductive substrate layer 108b, or may have a different thickness depending on, for example, the structural rigidity requirements of the resulting conductive stiffener 100.

Further, according to some embodiments, the top of the conductive stiffener 100 can exclude the top conductive layer 102a. Rather, the conductive material 102 can form only the bottom conductive layer 102c and the conductive tube or hollow column 102b within the VIA 104. With only the bottom conductive layer 102c and the conductive tube or hollow column 102b, the conductive stiffener 100 still provides electrical and thermal conductivity to the top of the conductive stiffener 100.

Figure 2:
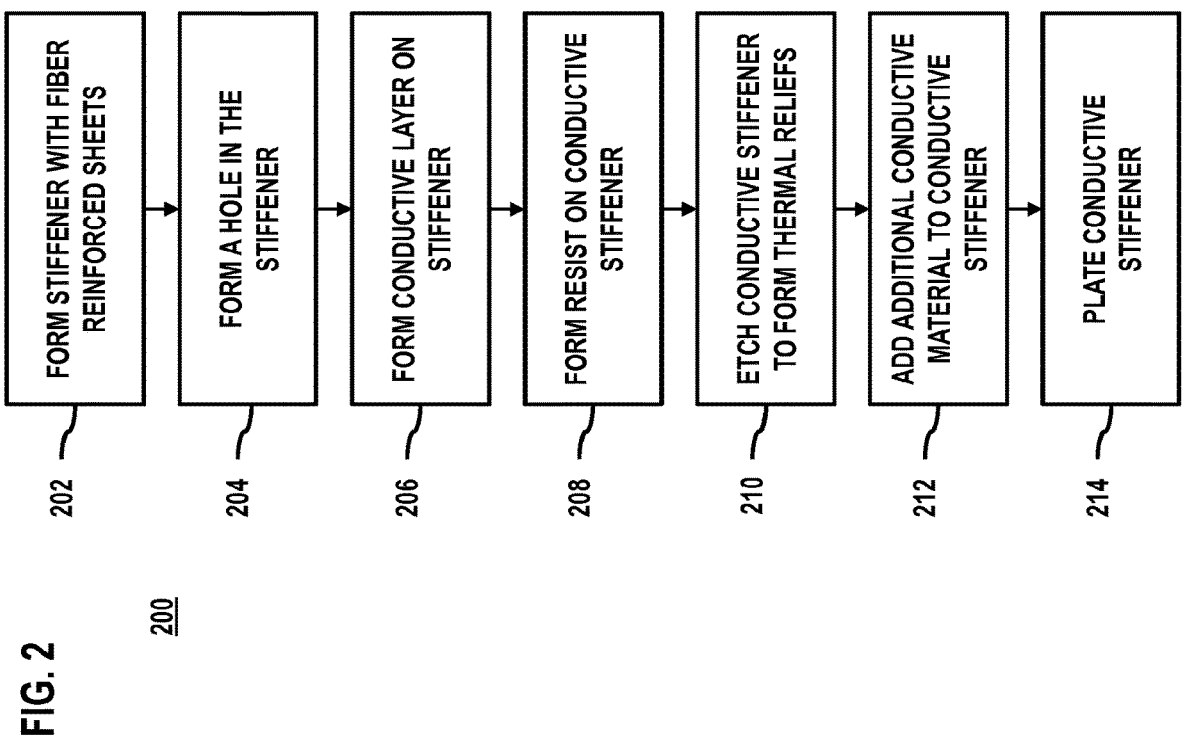
FIG. 2 shows a flow diagram of a process for making a conductive stiffener, in accord with aspects of the present concepts.

Referring to FIG. 2, FIG. 2 shows a flow diagram of a process 200 for making the conductive stiffener 100 illustrated in FIGS. 1A-1D, in accord with aspects of the invention. Although FIG. 2 illustrates and the following remarks describe the process 200 according to various acts in a specific sequence, the acts can be performed in varying sequences, and one or more acts can be added or omitted, without departing from the spirit and scope of the present disclosure.

Referring to step 202, the process 200 begins with adhering two non-conductive substrate sheets together with an adhesive to form a stiffener. The two non-conductive substrate sheets can be, for example, as described above with respect to the top non-conductive substrate sheet 108a and the bottom non-conductive substrate sheet 108b, the adhesive can be, for example, as described above with respect to the adhesive layer 110. In accordance with some embodiments, more than two non-conductive substrate sheets 108a, 108b . . . 108z can be adhered together using two or more adhesive layers 110.

At step 204, one or more holes can be formed through the stiffener to form a VIA. As stated above, a VIA can be formed anywhere on the stiffener; however, according to some embodiments, the VIA is formed in the middle of the stiffener. The VIA can be formed according to any conventional process for forming a VIA through the adhered non-conductive substrate layers, such as by drilling, punching, etching, etc.

At step 206, a conductive layer of conductive material can be formed on the exterior surfaces of the stiffener and lining the VIA. The conductive layer can be formed according to any conventional process, such as by plating, laminating, and/or using direct metallization, and can be formed to various thicknesses, such as 0.0007". As described above, the conductive material used can be, for example, copper, gold, silver, nickel, chrome, brass, bronze, and metal alloys. In accordance with some embodiments, the conductive material can be applied on the top and bottom of the stiffener and through the VIA, thus electrically and/or thermally connecting the top and bottom surfaces of the stiffener through the VIA.

At step 208, the conductive stiffener can be further processed by forming a resist layer (e.g., a light sensitive etch resist layer or photoresist layer) on the conductive stiffener in a pattern that defines thermal reliefs surrounding the VIA on one side of the conductive stiffener (e.g., the top side). According to some embodiments, the resist layer can be formed 0.002" thick to protect the conductive material that is intended to be left on the conductive stiffener after etching. The resist can be any suitable resist material used in the removal of the conductive material to form the thermal relief. By way of example, and with respect to copper as the conductive material, the resist material can be an ultraviolet light curing etch resistive material.

At step 210, the copper material exposed by the resist layer is then removed to form the thermal reliefs. According to some embodiments, and with respect to copper as the conductive material, the copper material can be removed by etching with ferric chloride, copper chloride or hydrochloric acid. After etching the conductive stiffener, the resist layer can be removed (e.g., by stripping) leaving the thermal relief pattern in the conductive material surrounding the VIA.

At step 212, after forming the thermal reliefs, additional conductive material can be formed on the remaining conductive material to thicken the conductive material surrounding the conductive stiffener. According to some embodiments, an additional 0.0007" of conductive material, such as copper, can be formed above the remaining conductive material. According to some embodiments, the additional conductive material added in step 212 can be the same conductive material original formed on the stiffener. According to some embodiments, the additional conductive material can be a different conductive material, such as gold, silver, nickel, chrome, or a metal alloy.

According to some embodiments, at step 214, the conductive stiffener can be plated using an electroless nickel immersion gold process to protect the conductive layers on the top and bottom surfaces of the conductive stiffener. Plating can occur to only one side of the conductive stiffener, such as the side opposite from the FPCB, to provide for optimal electrode conductivity. Alternatively, both sides can be plated using the electroless nickel immersion gold process. However, step 214 can be omitted, or the conductive stiffener can be exposed to a different process to protect the conductive layers on the top and bottom surfaces. After step 214, the conductive stiffener is ready for application to a FPCB assembly.

Although the process 200 is described with respect to forming a single conductive stiffener, according to some embodiments, multiple conductive stiffeners can be formed simultaneously through a single process. By way of example, and without limitation, the dimensions of the two non-conductive substrate sheets in step 202 can be large enough to form multiple conductive stiffeners simultaneously. After forming the conductive stiffeners using appropriately large enough non-conductive substrate sheets, the two conductive stiffeners can be separated by cutting the two non-conductive substrate sheets into the respective conductive stiffeners.

According to some embodiments, prior to separating the conductive stiffeners, the two non-conductive substrate sheets can be plated with tin and patterned with an additional resist based on a pattern of the conductive material for each conductive stiffener. The tin and conductive material left unprotected by the resist can be removed, such as by submerging the structure in an alkaline solution. After removing the unprotected material, the resist and remaining tin can be removed, such as through a striping process. The conductive stiffeners can then be separated into the individual stiffeners.

Referring to FIG. 3, FIG. 3 shows a flow diagram of a process 300 for attaching a conductive stiffener to an FPCB assembly, in accord with aspects of the present concepts. Although FIG. 3 illustrates and the following remarks describe the process 300 according to various acts in a specific sequence, the acts can be performed in varying sequences, and one or more acts can be added or omitted, without departing from the spirit and scope of the present disclosure.

At step 302, an adhesive layer is applied to the top surface of the conductive stiffener around the VIA and the thermal reliefs. The adhesive material used to form the adhesive layer can be any suitable adhesive used in the PCB and FPCB arts, such as, for example, a Pyralux® FRO200 adhesive, polyimide based adhesive or epoxy based adhesive. The adhesive layer can be any suitable thickness to attach the conductive stiffener, such as, for example, 0.002" thick. The adhesive layer can be formed around the VIA and the thermal reliefs of the VIA so as to provide room for solder to affix the conductive stiffener to the backside of a FPCB assembly.

At step 304, the conductive stiffener is adhered to the backside of the FPCB assembly by the adhesive layer. The adhesive layer at least partially attaches the conductive stiffener to the backside of the FPCB assembly. The conductive stiffener is adhered to the backside of the FPCB assembly such that the VIA of the conductive stiffener aligns with an electrical contact pad on the backside surface of the FPCB.

At step 306, the VIA is filled with solder (or another similar conductor) to complete the connection of the conductive stiffener to the backside of the FPCB assembly. The solder can be any suitable conductive material for attaching a stiffener to an FPCB assembly. Preferably the solder is a lead-free (e.g., tin or silver based solder) or other biocompatible solder to avoid incompatibility when the device is worn by a user. The conductive column and the solder within the VIA mechanically, electrically, and thermally connect the backside of the electrical component and the electrical contact pad to the conductive pad on the bottom surface of the conductive stiffener. Accordingly, the conductive stiffener provides both structural rigidity at specific positions of the FPCB assembly and thermal and electrical conductivity to electrical components of the FPCB assembly.

Figure 4:
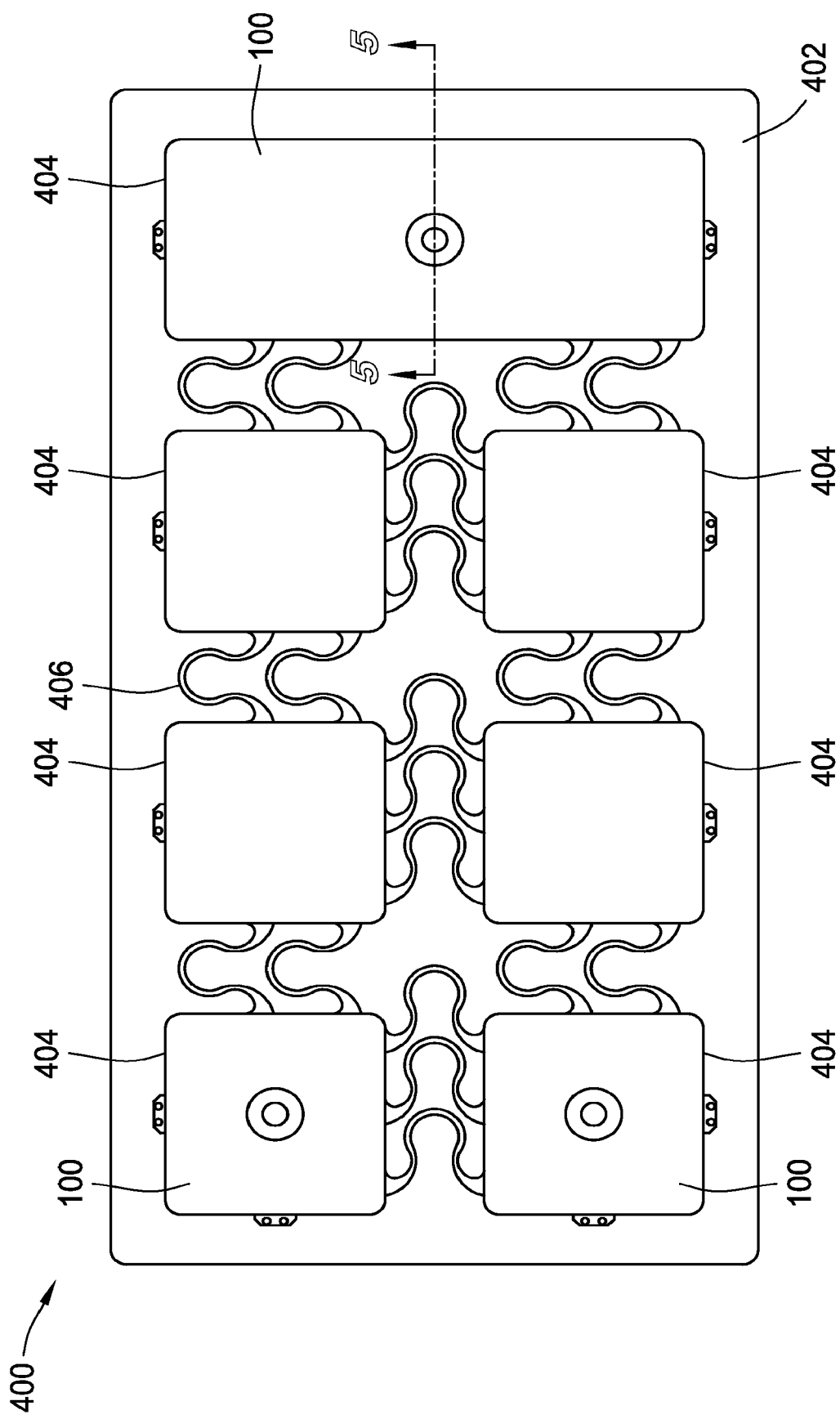
FIG. 4 shows a perspective view of a backside of a FPCB with attached conductive stiffener, in accord with aspects of the present concepts.

Referring to FIG. 4, FIG. 4 shows a perspective view of a backside of a FPCB assembly 400 with attached conductive stiffeners 100, in accord with aspects of the present concepts. As shown, the FPCB assembly 400 includes FPCB sections arranged in device islands 404 and surrounded by or encapsulated in a flexible polymer or elastomer substrate 402. The FPCB sections can be any conventional non-conductive or dielectric substrate for a FPCB, such as a polyimide and/or a silicone. The FPCB sections can include copper circuit traces and pads to facilitate attachment of electrical components, such as by soldering. By way of example, and without limitation, the electrical components can be any discrete operative device embedded in and/or affixed to the FPCB substrate 402, such as one or more microprocessors, microcontrollers, system on a chip devices, physical sensors (e.g., accelerometers, gyros, or inertial navigation sensors), biological and/or chemical sensors, active pixel sensors, amplifiers, analog-to-digital (A/D) converters, digital-to-analog (D/A) converters, optical sensors (e.g., photodiodes, photoresistors, CCD sensors), electro-mechanical transducers (e.g., MEMS sensors), piezoelectric sensors and actuators, light emitting diodes (LEDs), light emitting electronics, thermistors, thermocouples, memory devices, clock devices, active matrix switches, integrated circuits, resistors, capacitors, or other similar discrete operative devices. The FPCB assembly 400 can be constructed from two or more electrically interconnected device islands 404, each device island 404 including one or more electronic components embedded in or affixed to the FPCB. The device islands 404 can be interconnected by wires or interconnects 406. According to some embodiments, the interconnects 406 can be bendable and/or stretchable interconnects to accommodate the flexible, bendable, stretchable and conformal properties of the FPCB assembly 400, while also maintaining an electrical interconnection between two or more electrical components 404, such as two adjacent device islands 404, while in use.

The FPCB assembly 400 shown in FIG. 4 includes seven device islands 404, with the right most and two left most device islands 404 including conductive stiffeners 100 in accordance with some embodiments of the invention. Specifically, two conductive stiffeners 100 are aligned with and attached to the two leftmost device islands 404, and one larger conductive stiffener 100 is aligned with and attached to the rightmost device island 404. In accordance with some embodiments of the invention, the conductive stiffeners 100 can have the same shape as the device island 404 that the conductive stiffener 100 is attached is connected to. In accordance with some embodiments of the invention, the conductive stiffener 100 can larger or smaller (e.g., in one or two dimensions) than the device island 404 that it is attached to. Accordingly, the conductive stiffeners 100 provide stiffness as needed across the various FPCB sections and protect the device islands 404 from damage caused by bending of the FPCB assembly 400 (e.g., within certain limits). However, according to some embodiments, the conductive stiffener 100 can be slightly larger or slightly smaller than the device island 404 to provide more or less structural rigidity at the electrical component and, for example, to ensure complete overlap between the conductive stiffener 100 and the device island 404 during bending of the FPCB assembly 400.

Figure 5:
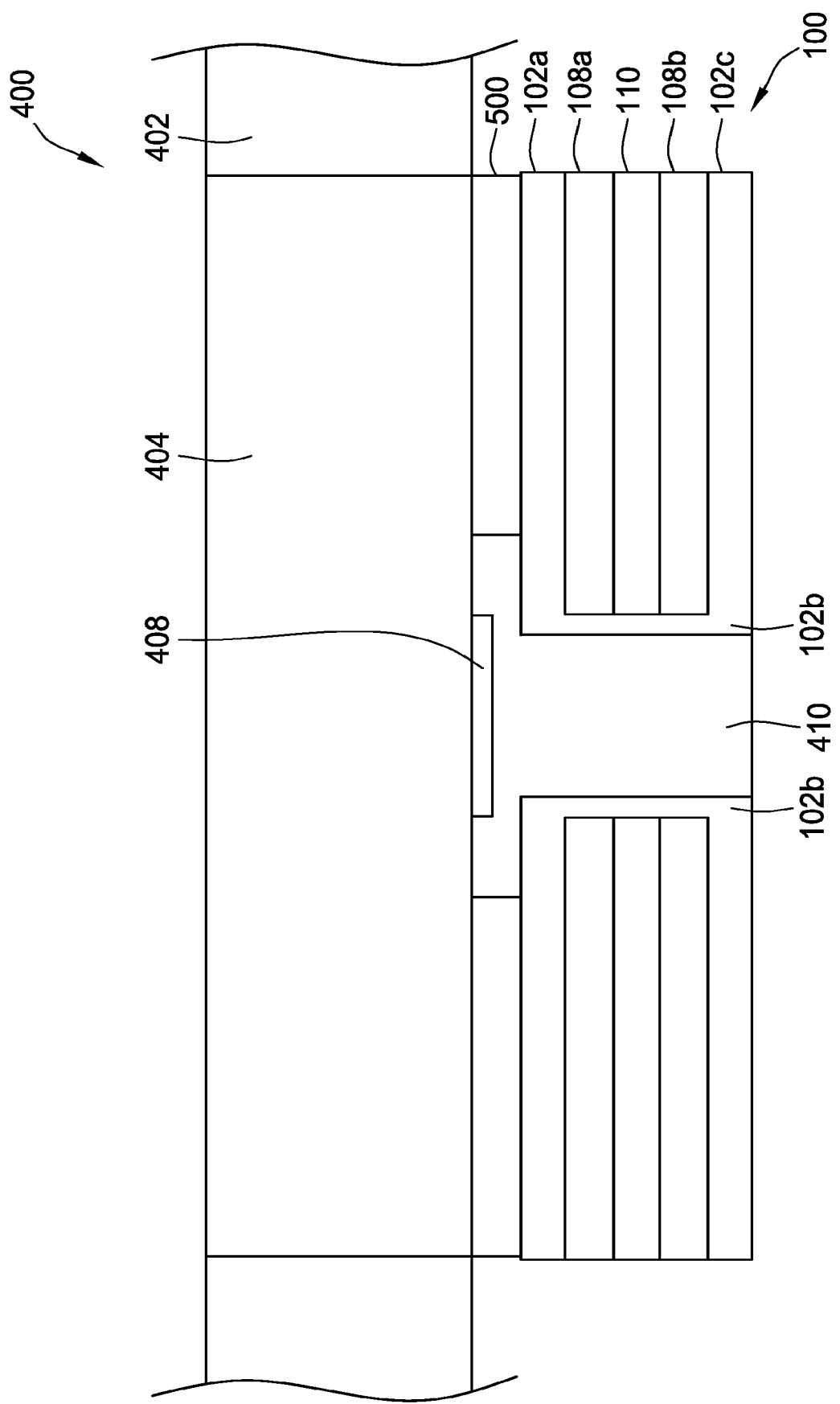
FIG. 5 shows a cross section of a FPCB with an attached conductive stiffener along the line 5-5 in FIG. 4, in accord with aspects of the present concepts.

FIG. 5 shows a cross section of a FPCB assembly 400 with the attached conductive stiffener 100 along the line 5-5 in FIG. 4, in accord with aspects of the present concepts. In accordance with some embodiments, the conductive stiffener 100 can include the top conductive layer 102b and the bottom conductive layer 102c, with the top non-conductive substrate layer 108a and the bottom non-conductive substrate layer 108b sandwiching the adhesive layer 110. The conductive stiffener 100 can also include the conductive tube or hollow column 102b within the VIA 104.

As shown, the conductive stiffener 100 is below a device island 404 of the FPCB assembly 400. The device island 404 can include one or more conductive contact pads 408, such an electrical and/or a thermal conductive contact pad. The conductive stiffener 100 can be affixed to the backside of the device island 404 so that the VIA 104 of the conductive stiffener 100 is aligned with the contact pad 408. The conductive stiffener 100 can further include solder 410 that fills the VIA and mechanically and electrically connects the conductive stiffener 100 to one or more contact pads 408 of device island 404. The thermal reliefs 106 (not shown in FIG. 5) allow the solder to fill the remaining void within the VIA 104 while reducing the thermal strain during soldering.

The conductive stiffener 100 provides structural rigidity to the FPCB assembly 400 at one or more device islands 404 and also thermally and/or electrically connects the device island 404 to the conductive stiffener 100. Accordingly, with the conductive stiffener 100 installed, the FPCB assembly 400, and particularly the device island 404 of the FPCB assembly 400, does not need to be connected to external electrodes. Rather, the conductive stiffeners 100 function as the external electrodes while providing a slim profile that provides little to no resistance to the conformability of the FPCB assembly 400.

The resulting encapsulated FPCB assembly 400 together with the conductive stiffener 100 can be referred to as a wearable device or a patch. The wearable device can be placed directly in contact with the user (e.g., the user's tissue, such as skin and generate mechanical, electrical and/or thermal measurements of the user using the electrical components of the FPCB assembly 400 and through the conductive stiffener 100. According to some embodiments, the FPCB assembly 400 and the conductive stiffeners 100 can be placed directly on the biological surface (e.g., a tissue of the user such as skin, endothelial tissue, and epithelial tissue). However, according to some embodiments, to increase the adhesion of the resulting wearable device to a biological surface (e.g., the skin of a user), all or a portion of the bottom surface of the FPCB assembly 400 and conductive stiffeners 100 can be coated with an adhesive layer.

Figure 6:
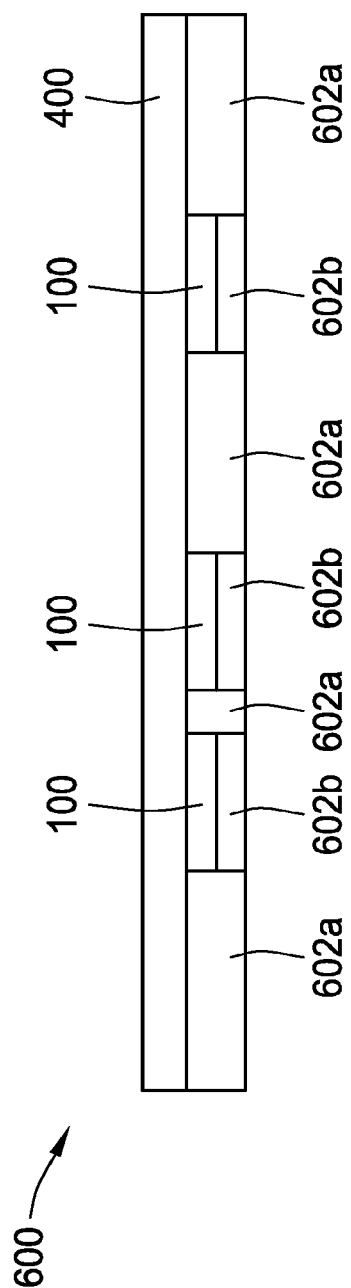
FIG. 6 shows a cross-section view of a wearable device, in accord with aspects of the present concepts.

FIG. 6 shows a cross-section view of a wearable device 600, in accord with aspects of the present concepts. The wearable device 600 includes the FPCB assembly 400 and multiple conductive stiffeners 100. The wearable device 600 can include an adhesive layer on one surface for attaching the device to a biological surface of the body. In accordance with some embodiments of the invention, the adhesive layer can be located on the bottom surface of the FPCB assembly 400 and surrounding the one or more conductive stiffeners 100 on three sides. The adhesive layer 602 can be any conventional adhesive layer used in adhering bandages and devices to the body, such as a silicone gel based adhesive or an acrylic based adhesive. In accordance with some embodiments, the adhesive layer 602 can be formed generally of a silicone adhesive. The adhesive layer 602 can include two different portions, a non-conductive adhesive portion 602a and a conductive portion 602b. The conductive portion 602b of the adhesive layer 602 permits electrical and/or thermal conduction through the adhesive layer 602. Accordingly, the conductive portions 602b can be positioned to align with the conductive stiffeners 100, and in some embodiments, the bottom conductive layers 102c of the conductive stiffeners 100, to allow thermal and electrical energy to pass through the adhesive layer 602 and reach the bottom conductive layers 102c of the conductive stiffeners 100. To isolate each respective conductive portion 602b, the adhesive layer 602 includes the non-conductive adhesive portions 602a that surround the conductive portions 602b. The non-conductive adhesive portions 602a are high impedance areas that prevent or substantially reduce the transmission of electrical energy and/or thermal energy there though. In accordance with some embodiments of the invention, the conductive The conductive portions 602b of the adhesive layer 602 provide a thermal and/or electrical conductive interface, where needed, between the biological surface and conductive stiffeners 100. Because the adhesive layer 602 includes the conductive portions 602b, the wearable device 600 can measure thermal and/or electric (e.g., biopotential and bioimpedance) signals, such as EMG, ECG, heart rate, galvanic skin response, and/or ECG tracking, among others, while having adhesive properties to aid the wearable device 600 in remaining coupled to the user. Accordingly, the adhesive layer 602 aids the wearable device 600 in remaining coupled to the user during the various activities in which the wearable device 600 monitors the physical and biological signals of the user, such as during exercising, sleeping, etc. For example, the conformal and flexible nature of the wearable device 600 allow for it to be placed on various parts of the body to monitor, for example, muscle activities.

Figure 7:
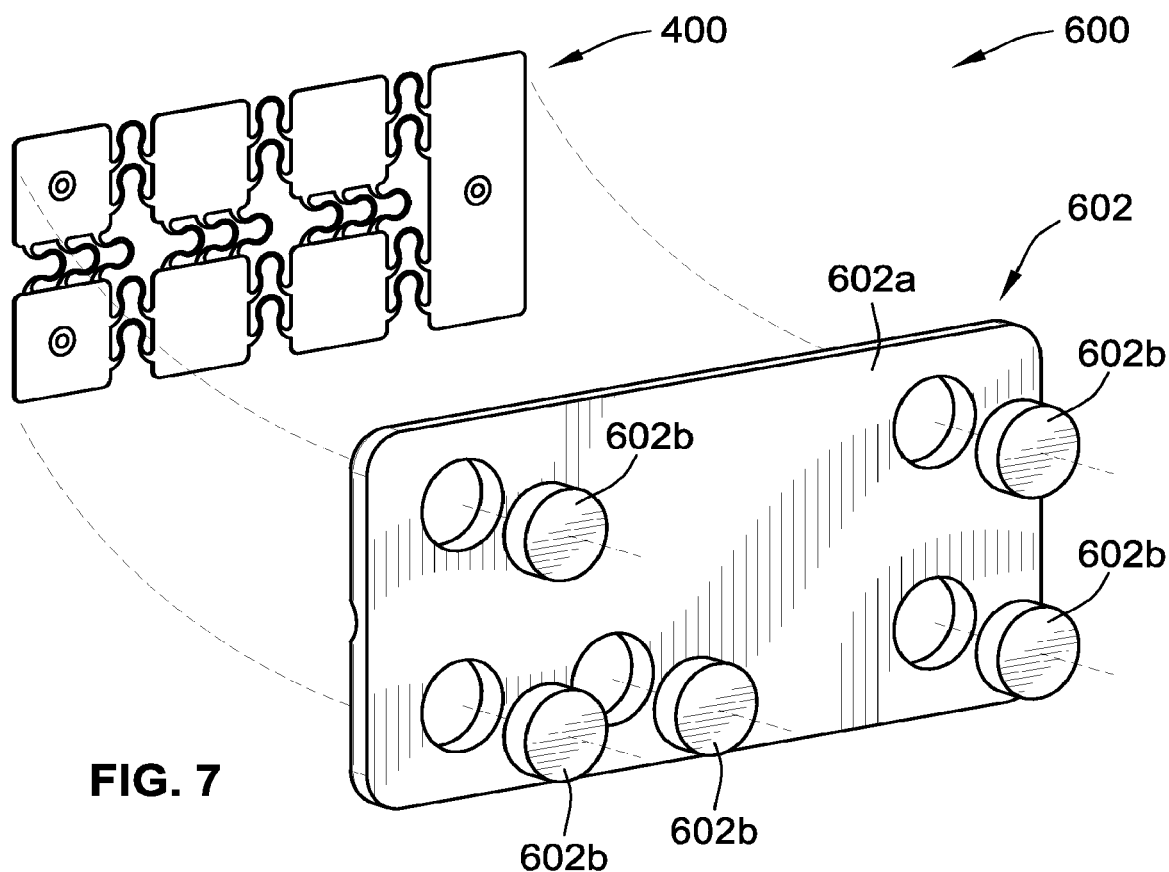
FIG. 7 shows an exploded perspective view of the wearable device of FIG. 6, in accord with aspects of the present concepts.
Figure 8:
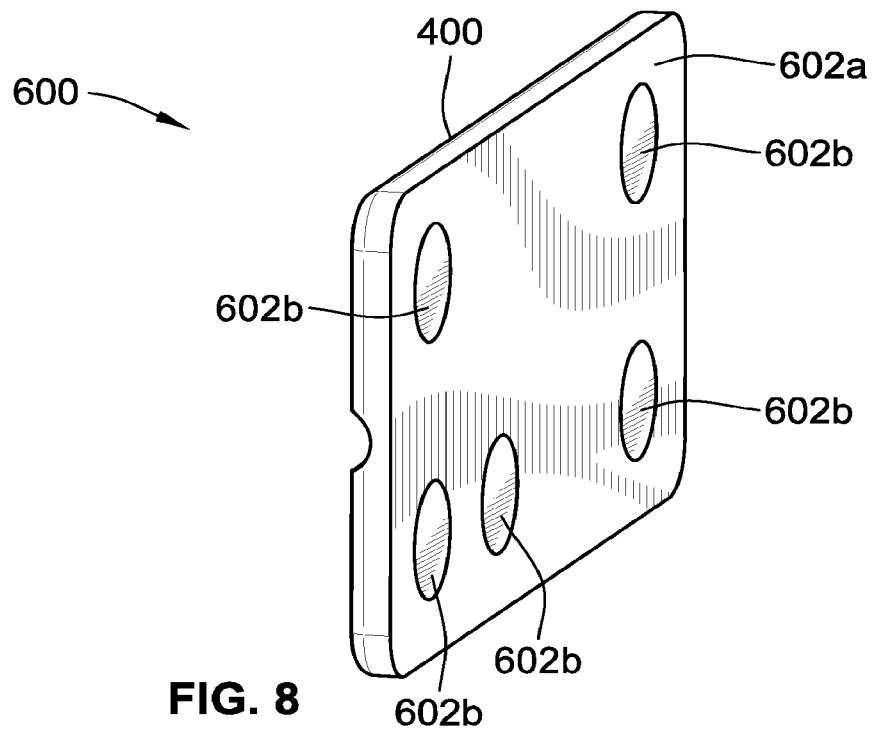
FIG. 8 shows an isometric view of the wearable device of FIGS. 6 and 7, in accord with aspects of the present concepts.

FIG. 7 shows an exploded perspective view of the wearable device 600 of FIG. 6, in accord with aspects of the present concepts, and FIG. 8 shows an isometric view of the wearable device 600 of FIGS. 6 and 7, in accord with aspects of the present concepts. As shown, the wearable device 600 includes the FPCB assembly 400, including the conductive stiffeners 100, on a top surface. The FPCB assembly 400 includes an adhesive layer 602. The adhesive layer 602 is generally comprised of the non-conductive adhesive portion 602*a* surrounding the conductive portions 602*b*. The conductive portions 602*b* align with the conductive stiffeners 100 to allow the conductive stiffeners 100 to receive electrical and/or thermal energy from a biological surface below the adhesive layer 602.

Although the conductive portions 602*b* of the adhesive layer 602 are shown as separate elements of the adhesive layer 602 relative to the non-conductive adhesive portions 602*a*, the conductive portions 602*b* can be integral with the non-conductive portions 602*a*. According to some embodiments, the conductive portions 602*b* can be integral with the non-conductive portions 602*a* by combining the same adhesive material (as the non-conductive portions 602*a*) with material additives that make the conductive adhesive portions 602*b* conductive. By way of example, and without limitation, the adhesive layer 602 can be formed of a silicone adhesive, and the conductive adhesive portions 602*b* can include additives that make the silicone within these portions conductive. According to some embodiments, the additives used to create the conductive portions 602*b* electrically and/or thermally conductive include silver (Ag), gold (Au), carbon, graphite, nickel/graphite, silver/silver chloride (Ag/AgCl) and other conductive material additives. Consequently, the non-conductive adhesive portions 602*a* of the adhesive layer 602 lack the conductive additives and provide good insulating properties. The conductive silicone used to form the conductive adhesive portions 602*b* can be integrated into the adhesive layer 602 according to various methodologies, to form integral or non-integral conductive adhesive portions 602*b*, such as by potting, insert molding, gluing, snapping, etc.

The conductive portions 602*b* provide a conductive path through the adhesive layer 602 that protects and isolates the underlying circuitry (e.g., electrical components 404 and interconnects 406) from the external environment. The conductive path only exists in selected areas that couple directly to the conductive stiffeners 100 on the backside of the FPCB assembly 400. According to some embodiments, the conductive portions 602*b* have volume resistivity in the range of 70 ohm·cm to 0.003 ohm·cm.

Although illustrated and described above with respect to the FPCB assembly 400 that includes the conductive stiffeners 100, according to some embodiments, the wearable device 600 of FIGS. 6-8 can exclude the conductive stiffeners 100. For example, depending on the specific application of the wearable device 600, the wearable device 600 may not require the additional stiffness provided by the conductive stiffeners 100. Accordingly, the conductive stiffeners 100 can be omitted. Instead, the conductive portions 602*b* of the adhesive layer 602 can interface directly with, for example, the various contact pads 408 or conductive surfaces of the device islands 404 of the FPCB assembly 400. The conductive portions 602*b* of the adhesive layer 602 can be configured (e.g, by selecting the appropriate thermally or electrically conductive material) to transmit the thermal and/or electrical energy directly to the contact pads 408 of the device islands 404.

Figure 9A:
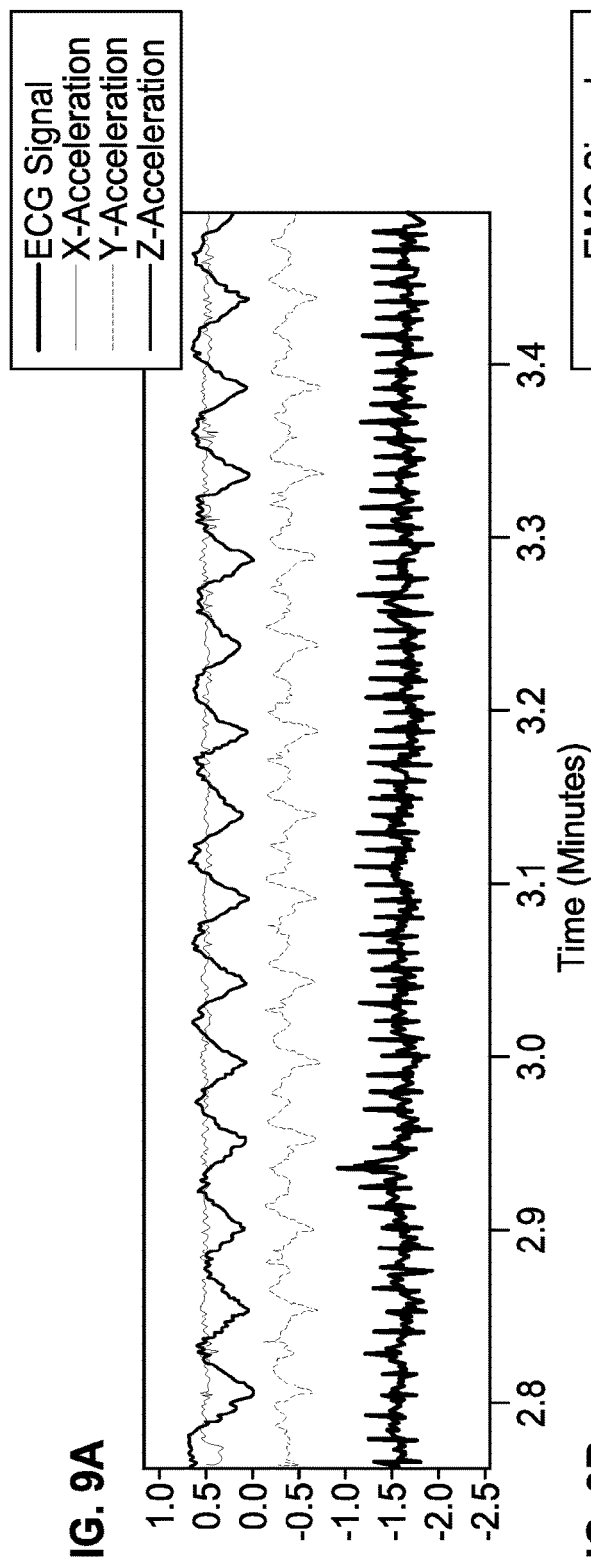
FIGS. 9A and 9B show biological signals generated by a wearable device, in accord with aspects of the present concepts.
Figure 9B:
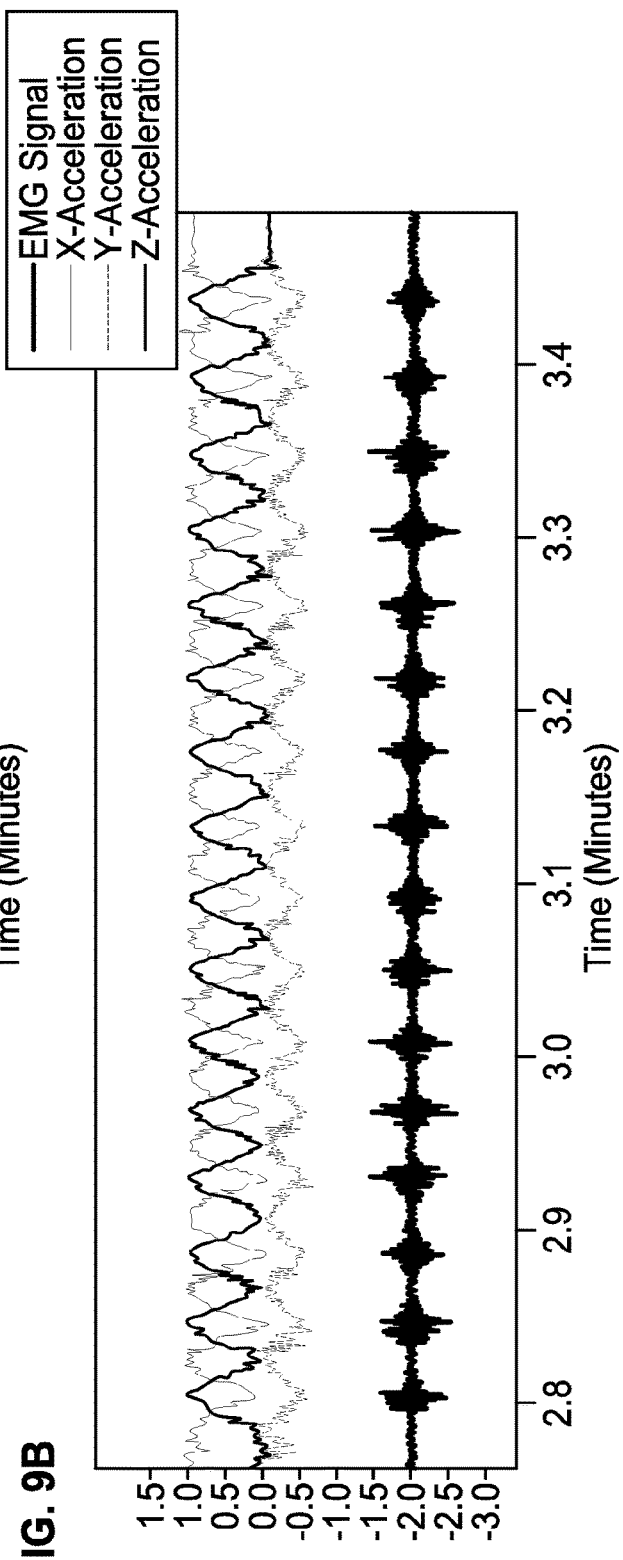

Referring to FIGS. 9A and 9B, these figures show the ability of the wearable device 600 located at various positions on a user to detect physical and biological electrical signals during use, in accord with aspects of the present concepts. Referring to FIG. 9A, the signals shown represent a wearable device 600 adhered to the chest of the user with the ability to measure acceleration in three axes (e.g., x, y, and z axes) and ECG signals. Referring to FIG. 9B, the signals shown represent a wearable device 600 adhered to the leg of the user with the ability to measure acceleration in three axes (e.g., x, y, and z axes) and EMG signals. In both figures, the user was performing squats as exemplary activity during which the signals are measured. As shown in FIGS. 9A and 9B, the wearable devices 600 are able to detect the biological signals from the user through the conductive portions 602*b*.

As an alternative to the adhesive layer 602 being placed only on the backside of the FPCB assembly 400, according to some embodiments, the FPCB assembly 400, with or without the conductive stiffeners 100, can be encapsulated within an encapsulation material to entirely protect the electrical components. Encapsulating the FPCB assembly 400 (and the conductive stiffeners 100) within the encapsulation layer seals off and protects the components from the elements of the outside environment during use, such as water, sweat, dirt, etc. Further, according to some embodiments, an encapsulation layer allows the resulting wearable device (e.g., a patch) to satisfy certain national and/or international standards or tests with respect to, for example, electrical devices and, more specifically, medical electrical devices. By way of example, an encapsulation layer allows a device to pass International Protection Marking tests.

Figure 10:
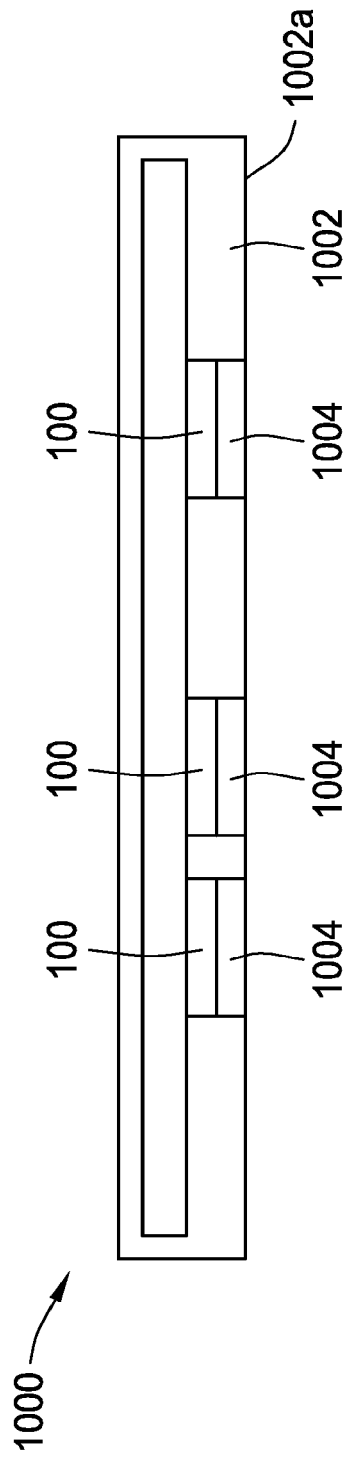
FIG. 10 shows a cross section view of a wearable device, in accord with aspects of the present concepts.

FIG. 10 shows a cross section view of a wearable device 1000, in accord with aspects of the present concepts. As shown, the wearable device 1000 includes the FPCB assembly 400 and multiple conductive stiffeners 100. However, according to some embodiments, and based on, for example, the application of the specific wearable device 1000, the wearable device 1000 may exclude the conductive stiffeners 100. As shown, the wearable device 1000 includes an encapsulation layer 1002 the entirely surrounds the FPCB assembly 400. A bottom surface 1002*a* of the encapsulation layer 1002 can include an adhesive layer, similar to the adhesive layer 602 discussed above, but that the encapsulation layer also is above the FPCB assembly 400. Accordingly, the encapsulation layer 1002 can be formed of various conformable materials used in encapsulating electronics, such a silicones. The encapsulation layer 1002 can be non-conductive to prevent, for example, electrical signals from short circuiting or affecting measurements of the electrical components of the FPCB assembly 400. However, the encapsulation layer 1002 includes conductive portions 1004 that transmit thermal and/or electrical energy through the encapsulation layer 1002. The conductive portions 1004 can be similar in construction and function as the conductive 602*b* of the adhesive layer 602, and similarly, the conductive portions 1004 can be aligned with the conductive stiffeners 100 or contact pads 408 of the FPCB assembly 400.

By encapsulating the FPCB assembly 400 within the encapsulation layer 1002, the wearable device 1000 permits, for example, the monitoring of physical and biological signals, such as EMG, ECG, etc., underwater. Moreover, by having the conductive portions 1004 integrated into the encapsulation layer 1002, and below the conductive stiffeners 100 or contact pads 408 of the device islands 404, the wearable device 1000 functions as an entirely integrated monitoring device that does not require, for example, additional electrodes tethered by wires to the FPCB assembly 400.

As disclosed above, and according to some embodiments, the adhesive layer 602 and the encapsulation layer 1002 can be generally applied to the FPCB assembly 400 such that, for example, the interface between the adhesive layer 602 or the encapsulation layer 1002 and the FPCB assembly 400, or components thereof, is a planar or smooth interface. However, according to some embodiments, features can be formed into the FPCB assembly 400 and/or the conductive stiffeners 100 to provide a more mechanically stable interface for the adhesive layer 602 or the encapsulation layer 1002.

Figure 11:
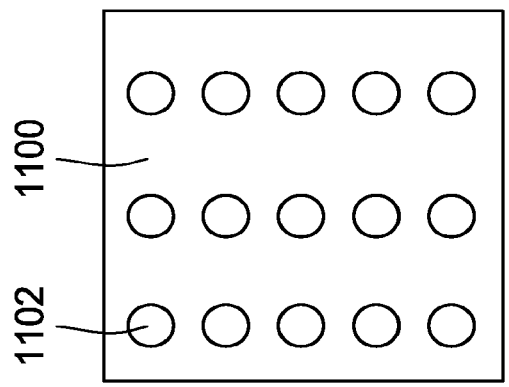
FIG. 11 shows a bottom view of features on a substrate to provide an improved interface, in accord with aspects of the present concepts.

Accordingly, FIG. 11 shows a bottom view of features 1102 formed on a substrate 1100 to provide an improved interface, in accord with aspects of the present concepts. Specifically, FIG. 11 shows a substrate 1100. The substrate 1100 can generally refer to a conductive stiffener 100, a device island 404 of the FPCB assembly 400, or the entire FPCB assembly 400. Thus, the substrate 1100 includes a surface that interfaces with the adhesive layer 602 or the encapsulation layer 1002.

To improve adhesion of, for example, the conductive adhesive portions 602b and the conductive portion 1004, the substrate 1100 can includes features 1102. According to some embodiments, the features 1102 can be VIAs formed in the substrate 1100. According to some embodiments, the VIAs can extend entirely through the substrate 1100, or may extend partially into the substrate 1100. The adhesive layer 602 or the encapsulation layer 1002 at least partially fills the VIAs to provide a larger contact area and greater mechanical adhesion to the substrate 1100. Thus, the features 1102 as VIAs provide some additional mechanical grip for the adhesive layer 602 or the encapsulation layer 1002 such that these layers do not have to solely rely on adhesion to a planar surface. Accordingly, the features 1102 applied to the FPCB assembly 400 and/or the conductive stiffeners 100 provide a better adhesive interface with the adhesive layer 602 and the encapsulation layer 1002 to improve the mechanical grip between the two different layers.

As alternatives to VIAs, the features 1102 may be any other type of protuberance and/or indentation on the substrate 1100 that alters the smooth surface of the substrate 1100 to something other than substantially smooth or planar. By way of example, and without limitation, according to some embodiments, the features 1102 can be pad rings that protrude beyond the surface of the substrate 1100. Alternatively, the features 1102 can be a combination of VIAs and pad rings surrounding the VIAs, such that the adhesive layer 602 or the encapsulation layer 1002 both extends into the VIAs and extends over the pads rings. Further, although a specific arrangement and number of features are illustrated in FIG. 11, the number and arrangement of the features 1102 can vary without departing from the spirit and scope of the present disclosure.

In addition or in the alternative to forming features in or on the FPCB assembly 400 of the conductive stiffeners 100 to improve adhesion with the adhesive layer 602 or the encapsulation layer 1002, according to some embodiments, the configuration of the FPCB assembly 400 can be changed.

Figure 12:
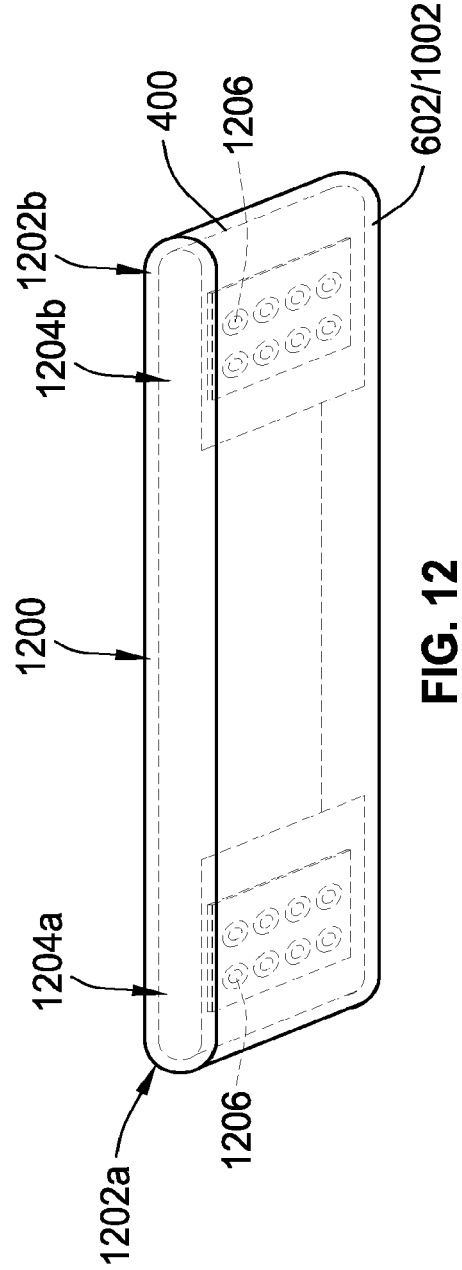
FIG. 12 shows an exemplary configuration of a FPCB to improve mechanical adhesion, in accord with some aspects of the present concepts.

FIG. 12 shows an exemplary configuration of a FPCB assembly 400 to improve mechanical adhesion to the FPCB assembly 400, in accord with some aspects of the present concepts. FIG. 12 includes a FPCB assembly 400 that has its ends 1202a and 1202b folded to form pockets 1204a and 1204b between the folded ends 1202a and 1202b and the main body 1200 of the FPCB assembly 400. The pockets 1204a and 1204b sandwich the material of the adhesive layer 602 or the encapsulation layer 1002 between the pockets 1204a and 1204b and the main body 1202. By sandwiching the material, the configuration of the FPCB assembly 400 provides additional mechanical strength and/or resistance to the adhesive layer 602 or the encapsulation layer 1002 from being removed from the FPCB assembly 400.

According to some embodiments, and as illustrated in FIG. 12, the ends 1202a and 1202b can also include VIAs 1206. The VIAs 1206 can be through only the FPCB assembly 400, or the VIAs 1206 can be through the FPCB assembly 400 and conductive stiffeners 100 located at the ends 1202a and 1202b of the FPCB assembly 400. When the pockets 1204a and 1204b are filled with the material of the adhesive layer 602 or the encapsulation layer 1002, the material flows from inside the pockets 1204a and 1204b and through the VIAs 1206 to outside of the pockets 1204a and 1204b. The material through the VIAs 1206 provides additional mechanical contact with FPCB assembly 400 such that the material of the adhesive layer 602 or the encapsulation layer 1002 does not rely solely on its adhesion to the planar surface of the FPCB assembly 400. Additionally, the VIAs 1206 can be electrically connected to electrical components 404 of the FPCB assembly 400, and the material that flows through the VIAs 1206 can be the conductive material that forms the conductive adhesive portions 602b of the adhesive layer 602 or the conductive portion 1004 of the encapsulation layer 1002. Thus, the point of mechanical contact can also be a point of electrical contact between the adhesive layer 602/encapsulation layer 1002 and the FPCB assembly 400.

The adhesive layer 602 or the encapsulation layer 1002 under the main body 1200 can be filled to form a substantially planer surface of the adhesive layer 602 or the encapsulation layer 1002 on the backside of the FPCB assembly 400 to form the wearable device 600 or 1000. Thus, the surface that contacts the biological surface can still be substantially planar. Further, although both ends 1202a and 1202b are shown in FIG. 12 as folded to form the pockets 1204a and 1204, according to some embodiments, only one end (e.g., 1202a or 1202b) can be folded to form a pocket (e.g., 1204a or 1204b) in the FPCB assembly 400.

Figure 13A:
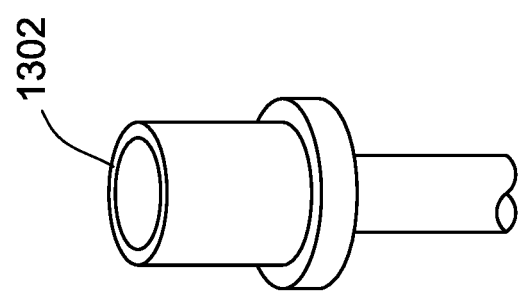
FIG. 13A shows an exemplary swage pin, in accord with some aspects of the present concepts.
Figure 13B:
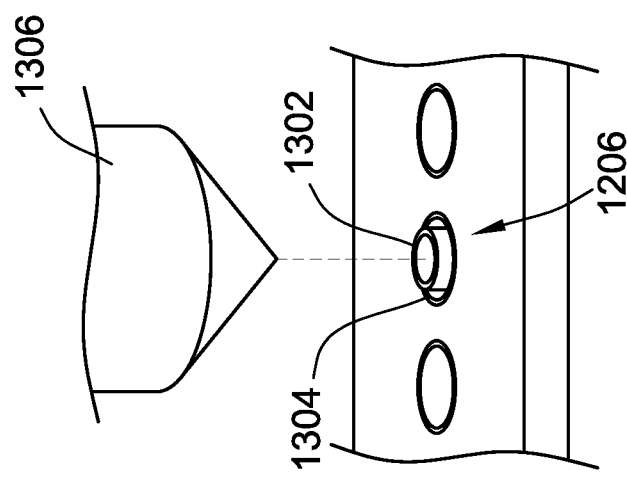
FIG. 13B shows the exemplary swage pin of FIG. 13A inserted within a VIA, in accord with some aspects of the present concepts.
Figure 13C:
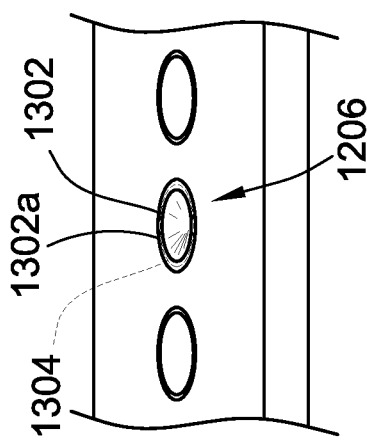
FIG. 13C shows the exemplary swage pin of FIG. 13A fastened within the VIA of FIG. 13B by deformation, in accord with aspects of the present concepts.

FIGS. 13A-13C show an exemplary and optional configuration of the VIAs 1206 for electrical and mechanical contact, in accord with some aspects of the present concepts. Specifically, electrical and mechanical contact can be further improved by application of an electrically conductive insert within the VIA 1206. Such an insert can be, for example, an electrically conductive rivet or swage pin 1302 (FIGS. 13A-13C). The electrically conductive insert can interface with a conductive ring 1304 (FIGS. 13B and 13C) around the VIA 1206 at the surface. Application of the electrically conductive insert into the VIA 1206 can cause the insert to contact the conductive ring 1304. In the example of the electrically conductive rivet or swage pin 1302 as the insert, the rivet or swage pin 1302 can be applied using an arbor press (not shown) and swage punch 1306 (FIG. 13B) through the VIA 1206, with the resulting flared portion 1302a of the rivet or swage pin 1302 contacting the conductive ring 1304 (FIGS. 13B and 13C) to provide electrical contact to the rivet or swage pin 1302 after swaging.

The various wearable devices disclosed above are fully-functional skin-mountable devices with conductive stiffeners functioning as integrated single-channel or multi-channel electrodes. The conductive stiffeners also provide mechanical stability for the electrical components on the top side of the FPCB. The arrangement of the conductive stiffeners and the adhesive layer or encapsulation layer reduces the overall thickness of the resulting skin-mountable wearable device, while also simplifying the manufacturing process in which electrode functionality is required.

Including conductive stiffeners on the backside surface of FPCB and aligned with contact pads of electronic components of the FPCB provides both mechanical and electrical functionalities and benefits. For example, the conductive stiffeners provide mechanical stability to the backside of surface mounted or embedded electronic components in FPCB for mechanical reliability purposes. Further, the conductive stiffeners provide an electrically conductive medium on the backside of FPCB with conductive adhesive contact directly with skin or any other soft biological tissue. The conductive stiffeners also provide a thermally conductive medium on the backside of the FPCB for thermal relief and/or temperature sensing of the surface mounted or embedded electronic components.

According to some embodiments, combining the conductive stiffener with the FPCB combines two elements and reduces the total number of parts and instructions for use that are required to measure, for example, electrical activity from a biological surface. The reduction in the number of components and complexity manifest in less noisy signal quality because of, for example, the reduced electrical length between the sensor (e.g., the bottom conductive layer of the conductive stiffener) and the receiver (e.g., the electrical component). The reduced electrical length eliminates sources of noise, such as 60 Hz noise from power lines and motion artifacts from movement.

In addition to sensing, the conductive stiffeners also can provide sites for active alternating current (AC) and/or direct current (DC) stimuli to be applied to the skin, peripheral nerves, or any other soft biological site. The conductive stiffeners also allow for charging a skin-mounted wearable device using the conductive surfaces as the charging interfaces.

While particular embodiments and applications of the present disclosure have been illustrated and described, it is to be understood that the present disclosure is not limited to the precise construction and compositions disclosed herein and that various modifications, changes, and variations can be apparent from the foregoing descriptions without departing from the spirit and scope of the invention as defined in the appended claims.

What is claimed is:

1. A device comprising:
   a flexible printed circuit board having a plurality of discrete operative devices electrically interconnected and one or more contact pads on a backside of the flexible printed circuit board; and
   a plurality of conductive stiffeners affixed to the backside of the flexible printed circuit board, each conductive stiffener electrically connecting at least one contact pad of the flexible printed circuit board to a bottom surface of the conductive stiffener and comprising:
   a non-conductive substrate sheet;
   a hole through the non-conductive substrate sheet; and
   a conductive material forming a pad on a bottom surface of the non-conductive substrate sheet and lining the hole, wherein the pad of conductive material is electrically connected to a top surface of the non-conductive substrate sheet through the conductive material lining the hole,
   wherein the conductive material forms a pad on the top surface of the non-conductive substrate sheet, and the pad of conductive material on the top surface comprises a thermal relief pattern in the conductive material surrounding the hole.

2. The device of claim 1, further comprising an encapsulation layer encapsulating the flexible printed circuit board and the plurality of conductive stiffeners.

3. The device of claim 2, wherein the encapsulation layer comprises non-conductive areas surrounding conductive areas, and the conductive areas are aligned with the bottom surfaces of the conductive stiffeners.

4. The device of claim 2, wherein a bottom surface of each conductive stiffener includes one or more indentations that interface with the encapsulation layer to mechanically couple the encapsulation layer to the plurality of conductive stiffeners.

5. The device of claim 4, wherein the one or more indentations are vertical interconnects accesses.

6. The device of claim 2, wherein a bottom surface of the flexible printed circuit board includes one or more indentations that interface with the encapsulation layer to mechanically couple the encapsulation layer to the flexible printed circuit board.

7. The device of claim 2, wherein at least one end of the flexible printed circuit board is folded creating a pocket, and the pocket is filled with encapsulation material forming the encapsulation layer to mechanically couple the encapsulation layer to the flexible printed circuit board.

8. The device of claim 7, wherein the at least one end of the flexible printed circuit board includes one or more vertical interconnect accesses, and the encapsulation material fills the one or more vertical interconnect accesses from the pocket through the at least one end to mechanically couple the encapsulation layer to the flexible printed circuit board.

9. The device of claim 1, wherein each of the conductive stiffeners includes a vertical interconnect access (VIA) through which the conductive stiffeners attach to the corresponding discrete operative device.

10. The device of claim 1, wherein the non-conductive substrate sheet is comprised of at least two FR-4 glass-reinforced epoxy laminate sheets.

11. The device of claim 10, wherein each sheet of the at least two sheets is 0.002 inches thick.

12. The device of claim 10, wherein the at least two sheets are adhered together with an adhesive layer.

13. The device of claim 12, wherein the adhesive layer is 0.002 inches thick.

14. The device of claim 1, wherein the conductive material is selected from a group consisting of copper, tin, nickel, silver, and gold.

15. The device of claim 1, wherein the pad of conductive material on the bottom surface is 0.0014 inches thick.

16. The device of claim 1, wherein the pad of conductive material on the top surface is 0.0014 inches thick.

17. A device comprising:
   a flexible printed circuit board having a plurality of discrete operative devices electrically interconnected and one or more contact pads on a backside of the flexible printed circuit board; and
   a plurality of conductive stiffeners affixed to the backside of the flexible printed circuit board, each conductive stiffener electrically connecting at least one contact pad of the flexible printed circuit board to a bottom surface of the conductive stiffener and comprising:
   a non-conductive substrate sheet;

a hole through the non-conductive substrate sheet; and a conductive material forming a pad on a bottom surface of the non-conductive substrate sheet and lining the hole, wherein the pad of conductive material is electrically connected to a top surface of the non-conductive substrate sheet through the conductive material lining the hole, wherein the conductive material forms a pad on the top surface of the non-conductive substrate sheet, and the pad of conductive material on the top surface is 0.0014 inches thick.

18. The device of claim 17, further comprising an encapsulation layer encapsulating the flexible printed circuit board and the plurality of conductive stiffeners.

19. The device of claim 18, wherein the encapsulation layer comprises non-conductive areas surrounding conductive areas, and the conductive areas are aligned with the bottom surfaces of the conductive stiffeners.

20. The device of claim 18, wherein a bottom surface of each conductive stiffener includes one or more indentations that interface with the encapsulation layer to mechanically couple the encapsulation layer to the plurality of conductive stiffeners.

21. The device of claim 20, wherein the one or more indentations are vertical interconnects accesses.

22. The device of claim 21, wherein a bottom surface of the flexible printed circuit board includes one or more indentations that interface with the encapsulation layer to mechanically couple the encapsulation layer to the flexible printed circuit board.

23. The device of claim 18, wherein at least one end of the flexible printed circuit board is folded creating a pocket, and the pocket is filled with encapsulation material forming the encapsulation layer to mechanically couple the encapsulation layer to the flexible printed circuit board.

24. The device of claim 23, wherein the at least one end of the flexible printed circuit board includes one or more vertical interconnect accesses, and the encapsulation material fills the one or more vertical interconnect accesses from the pocket through the at least one end to mechanically couple the encapsulation layer to the flexible printed circuit board.

25. The device of claim 17, wherein each of the conductive stiffeners includes a vertical interconnect access (VIA) through which the conductive stiffeners attach to the corresponding discrete operative device.

26. The device of claim 17, wherein the non-conductive substrate sheet is comprised of at least two FR-4 glass-reinforced epoxy laminate sheets.

27. The device of claim 26, wherein each sheet of the at least two sheets is 0.002 inches thick.

28. The device of claim 26, wherein the at least two sheets are adhered together with an adhesive layer.

29. The device of claim 28, wherein the adhesive layer is 0.002 inches thick.

30. The device of claim 17, wherein the conductive material is selected from a group consisting of copper, tin, nickel, silver, and gold.

31. The device of claim 17, wherein the pad of conductive material on the bottom surface is 0.0014 inches thick.

* * * * *